(12) United States Patent
Jelezko et al.

(10) Patent No.: US 10,107,874 B2
(45) Date of Patent: Oct. 23, 2018

(54) SENSOR COMPRISING A PIEZOMAGNETIC OR PIEZOELECTRIC ELEMENT ON A DIAMOND SUBSTRATE WITH A COLOUR CENTRE

(71) Applicant: ELEMENT SIX TECHNOLOGIES LIMITED, Didcot (GB)

(72) Inventors: Fedor Jelezko, Ulm (DE); Jianming Cai, Neu-Ulm (DE); Martin Plenio, Ulm (DE)

(73) Assignee: Element Six Technologies Limited, Didcot, Oxfordshire (GB)

( * ) Notice: Subject to any disclaimer, the term of this patent is extended or adjusted under 35 U.S.C. 154(b) by 52 days.

(21) Appl. No.: 15/304,320

(22) PCT Filed: Apr. 16, 2014

(86) PCT No.: PCT/EP2014/057788
§ 371 (c)(1),
(2) Date: Oct. 14, 2016

(87) PCT Pub. No.: WO2015/158383
PCT Pub. Date: Oct. 22, 2015

(65) Prior Publication Data
US 2017/0045591 A1 Feb. 16, 2017

(51) Int. Cl.
*G01R 33/032* (2006.01)
*G01N 24/10* (2006.01)
(Continued)

(52) U.S. Cl.
CPC ............ *G01R 33/032* (2013.01); *G01K 5/72* (2013.01); *G01N 21/66* (2013.01); *G01N 24/10* (2013.01);
(Continued)

(58) Field of Classification Search
CPC .............. G01R 33/0327; G01R 33/032; G01R 33/0322; G01R 33/26; G01R 33/24
(Continued)

(56) References Cited

U.S. PATENT DOCUMENTS 5,059,783 A * 10/1991 Stranjord ............. G01R 33/032
250/227.19
5,087,810 A * 2/1992 Carome ............... G01R 15/248
250/227.21
(Continued)

FOREIGN PATENT DOCUMENTS

DE 102010001144 A1 7/2011

OTHER PUBLICATIONS

MacQuarrie, E. R., et al. "Mechanical spin control of nitrogen-vacancy centers in diamond." Physical review letters 111.22 (2013): 227602.*
(Continued)

*Primary Examiner* — Christopher McAndrew
(74) *Attorney, Agent, or Firm* — Dean W. Russell; Clark F. Weight; Kilpatrick Townsend & Stockton LLP

(57) ABSTRACT

A sensor (1, 2, 3, 4, 5, 6, 7, 8) comprising a first diamond substrate (9) with at least one color center (15), the sensor (1, 2, 3, 4, 5, 6, 7, 8) further comprising a first piezomagnetic (10) or piezoelectric primary element (11), which primary element (10, 11) is arranged to interact with the color center(s) (15) of the first diamond substrate (9).

20 Claims, 17 Drawing Sheets

(51) Int. Cl.

| | |
|---|---|
| *G01R 33/60* | (2006.01) |
| *G01K 5/72* | (2006.01) |
| *G01N 21/66* | (2006.01) |
| *H01L 41/113* | (2006.01) |
| *H01L 41/187* | (2006.01) |
| *G01R 33/24* | (2006.01) |
| *G01R 33/26* | (2006.01) |

(52) U.S. Cl.
CPC .......... *G01R 33/60* (2013.01); *H01L 41/1132* (2013.01); *H01L 41/187* (2013.01); *G01R 33/0322* (2013.01); *G01R 33/0327* (2013.01); *G01R 33/24* (2013.01); *G01R 33/26* (2013.01)

(58) Field of Classification Search
USPC ...................................................... 324/244.1
See application file for complete search history.

(56) References Cited

U.S. PATENT DOCUMENTS

| | | | | |
|---|---|---|---|---|
| 6,972,562 | B1* | 12/2005 | Vlasko-Vlasov | G01Q 60/02 324/244.1 |
| 7,608,820 | B1* | 10/2009 | Berman | B82Y 35/00 250/306 |
| 8,362,762 | B2* | 1/2013 | Hokari | G01R 33/032 324/244.1 |
| 8,547,090 | B2* | 10/2013 | Lukin | G01R 33/032 324/244.1 |
| 9,378,880 | B2* | 6/2016 | Gangopadhyay | G01R 33/0322 |
| 2010/0264913 | A1* | 10/2010 | Sandhu | G01R 33/0213 324/214 |
| 2010/0308813 | A1* | 12/2010 | Lukin | G01R 33/032 324/244.1 |
| 2011/0304326 | A1* | 12/2011 | Sandhu | G01R 33/0213 324/214 |
| 2013/0038324 | A1* | 2/2013 | Wu | G01R 33/032 324/244.1 |

OTHER PUBLICATIONS

Zhao, Shi-feng, et al. "Magnetoelectric response analysis of the piezoelectric/piezomagnetic thin-film heterostructure derived by low energy cluster beam deposition." Piezoelectricity, Acoustic Waves, and Device Applications, 2008. SPAWDA 2008. Symposium on. IEEE, 2008.*

Doherty M W et al, "Electronic properties and metrology applications of the diamond NV—Center under pressure", Physical Review Letters, Jan. 31, 2014, vol. 112, No. 4, pp. 47601-1-47601-5, American Physical Society.

Schirhagl Romana et al, "Nitrogen-vacancy centers in diamond: nanoscale sensors for physics and biology", Annual Review of Physical Chemistry, 2014, vol. 65, pp. 83-105, Annual Reviews.

Dolde F et al, "Electric-field sensing using single diamond spins", Nature Physics, vol. 7, Jun. 2011, No. 6, pp. 459-463, Macmillan Publishers Limited.

Cai J et al, "Hybrid sensors based on colour centres in diamond and piezoactive layers", Nature Communications, Jun. 9, 2014, vol. 5, ISSN 2041-1723, pp. 1-6, Macmillan Publishers Limited.

Cai J. et al., "Signal transduction and conversion with color centers in diamond and piezo-elements", Internet Article, Cornell University Library, Apr. 25, 2014, Online, URL: http://arxiv.org/abs/1404.6393.

Gruber A et al, "Scanning Confocal Optical Microscopy and Magnetic Resonance on Single Defect Centers", vol. 276, Jun. 27, 1992, pp. 2012-2014, American Association of the Advancement of Science.

Jelezko F et al, "Observation of Coherent Oscillations in a Single Electron Spin", Phys. Rev. Lett., vol. 92, No. 7, pp. 076401-1-076401-4, Feb. 20, 2004, The American Physical Society.

Maze J R et al, "Nanoscale magnetic sensing with an individual electronic spin in diamond", Nature, vol. 455, pp. 644-647, Oct. 2, 2008, Macmillan Publishers Limited.

Balasubramanian G et al, "Nanoscale imaging magnetometry with diamond spins under ambient conditions", Nature, vol. 455, pp. 648-651, 2008, Oct. 2, 2008, Macmillan Publishers Limited.

Maletinsky P et al, "A robust scanning diamond sensor for nanoscale imaging with single NV centres", Nature Nanotechnology, vol. 7, pp. 320-324, May 2012, Macmillan Publishers Limited.

Rondin L et al, "Stray-field imaging of magnetic vortices with a single diamond spin", Nature Communications, vol. 4, pp. 2279-2283, Jul. 31, 2013, Macmillan Publishers Limited.

Muller C et al "Nuclear magnetic resonance spectroscopy and imaging with single spin sensitivity" Nature Communications, vol. 5, pp. 4703-4708, Aug. 22, 2014, Macmillan Publishers Limited.

Kucsko G et al, "Nanometre-scale thermometry in a living cell", Nature, vol. 500, pp. 54-59, Aug. 1, 2013, Macmillan Publishers Limited.

Toyli D et al, "Fluorescence thermometry enhanced by the quantum coherence of single spins in diamond", PNAS, vol. 110, pp. 8417-8421, May 21, 2013, Proceedings of the National Academy of Science of the United States of America.

Neumann P et al, "High-Precision Nanoscale Temperature Sensing Using Single Defects in Diamond", Nano Lett., vol. 13, pp. 2738-2742, May 30, 2013, American Chemical Society.

McGuinness L P et al, "Quantum measurement and orientation tracking of fluorescent nanodiamonds inside living cells", Nature Nanotechnology, vol. 6, pp. 358-363, Jun. 2011, Macmillan Publishers Limited.

Teraji T et al, "Chemical Vapor Deposition of 12C Isotopically Enriched Polycrystalline Diamond", Jpn. J. Appl. Phys., vol. 51, pp. 090104-1-090104-7, 2012, The Japanese Society of Applied Physics.

Ohno K et al, "Engineering shallow spins in diamond with nitrogen delta-doping", Appl. Phys. Lett., vol. 101, pp. 082413-1-082413-5, 2012, AIP Publishing.

Ohring M, "Materials Science of Thin Films: Deposition and Structure", 2001, Chapter 5, pp. 205-230, Academic Press.

Zhao B et al, "Preparation and optimization of ZnO films on single-crystal diamond substrate by metal-organic chemical vapour deposition", Semicond. Sci. Technol., vol. 19, pp. 770-773, 2004, IOP Publishing Ltd.

Buhlmann S et al, "Size effect in mesoscopic epitaxial ferroelectric structures: Increase of piezoelectric response with decreasing feature size", Appl. Phys. Lett., vol. 80, pp. 3195-3197, Apr. 29, 2002, AIP Publishing.

Lee K et al, "Two-dimensional planar size effects in epitaxial PbTiO3 thin films", Appl. Phys. Lett., vol. 85, No. 20, pp. 4711-4713, Nov. 15, 2004, AIP Publishing.

Wu C-W et al, "Electron-beam lithography assisted patterning of surfactant-templated mesoporous thin films", Nanotechnology, vol. 15, pp. 1886-1889, 2004, IOP Publishing Ltd.

Jelezko F et al, "Single defect centres in diamond: A review", Physica Status Solidi (a) Applications and Materials Science, vol. 203, No. 13, pp. 3207-3225, 2006, Wiley-VCH Verlag GmbH & Co. KGaA, Weinheim, Germany.

Jelezko F. et al., "Read-out of single spins by optical spectroscopy", Journal of Physics-Condensed Matter, vol. 16, pp. R1089-R1104, 2004, IOP Publishing Ltd.

Le Sage D el al, "Efficient photon detection from colour centres in a diamond optical waveguide", Phys. Rev. B, vol. 85, pp. 121202-1-121202-4, 2012, American Physical Society.

* cited by examiner

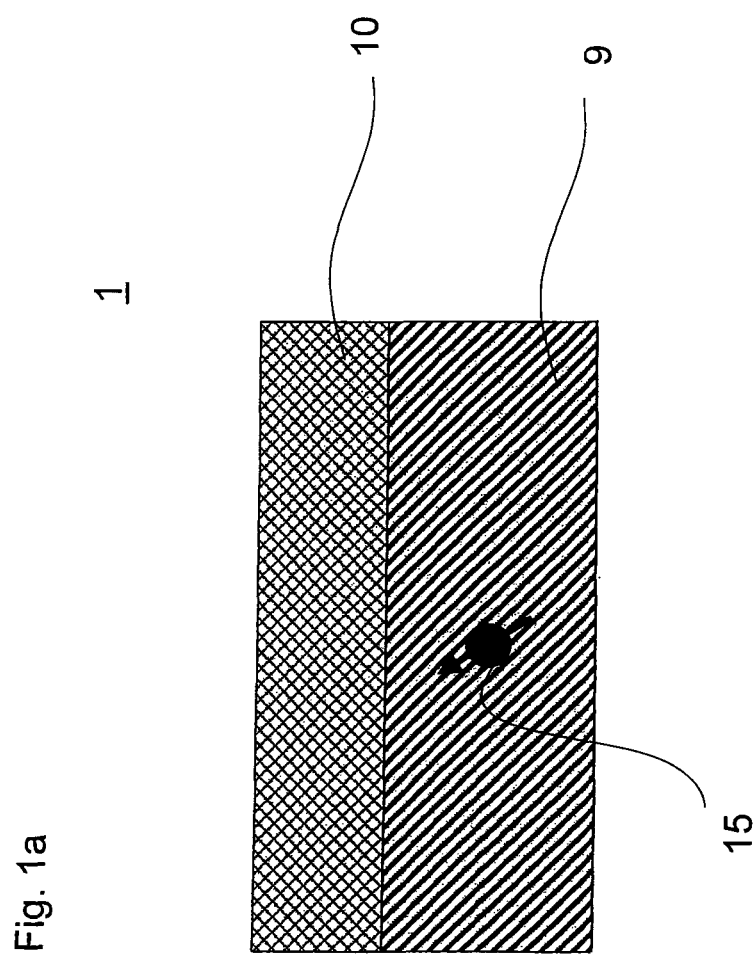

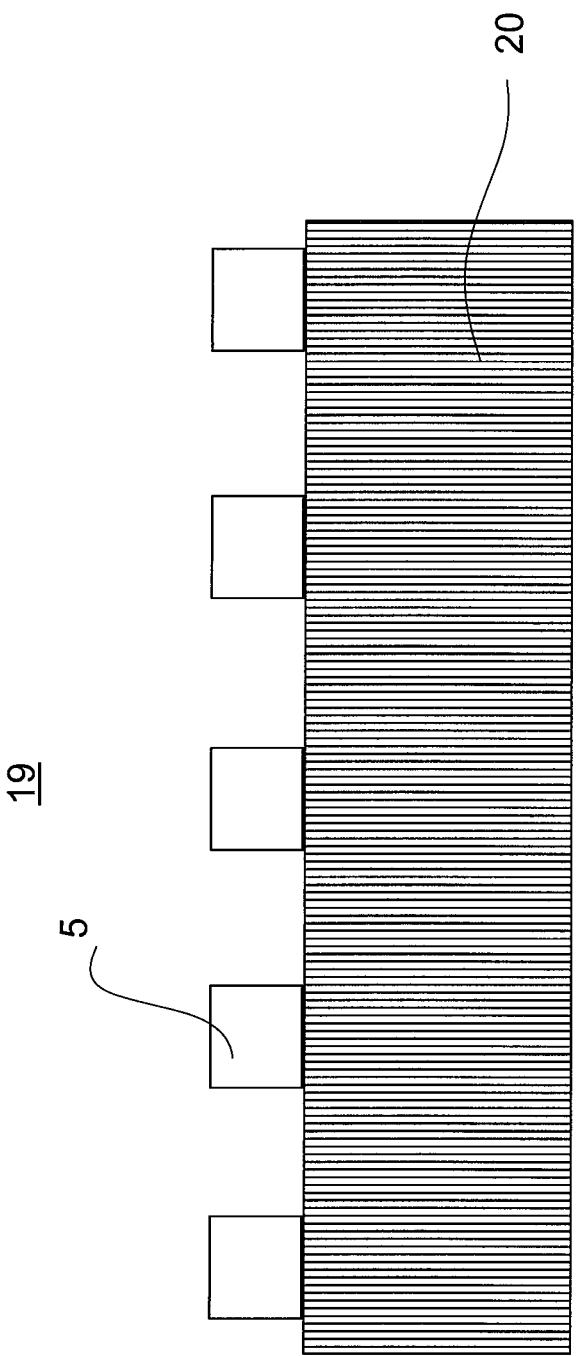

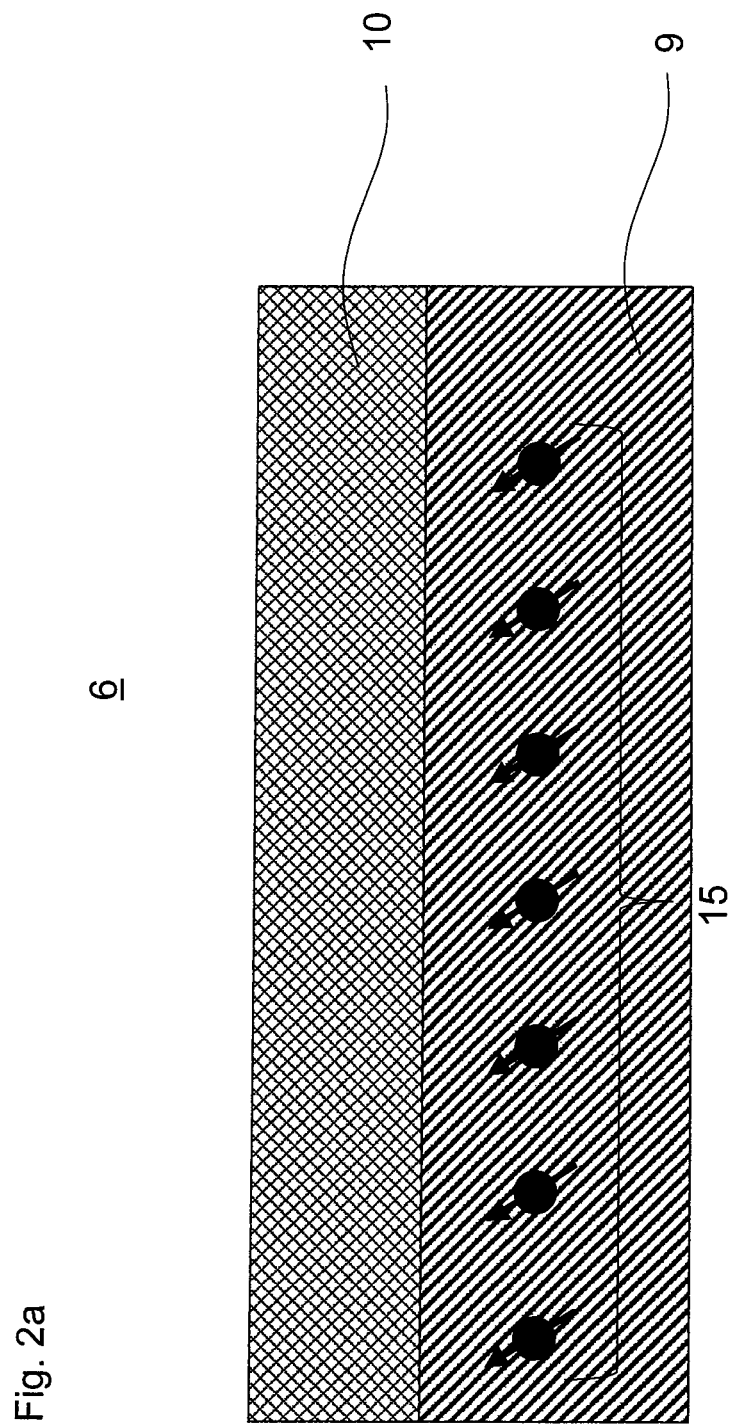

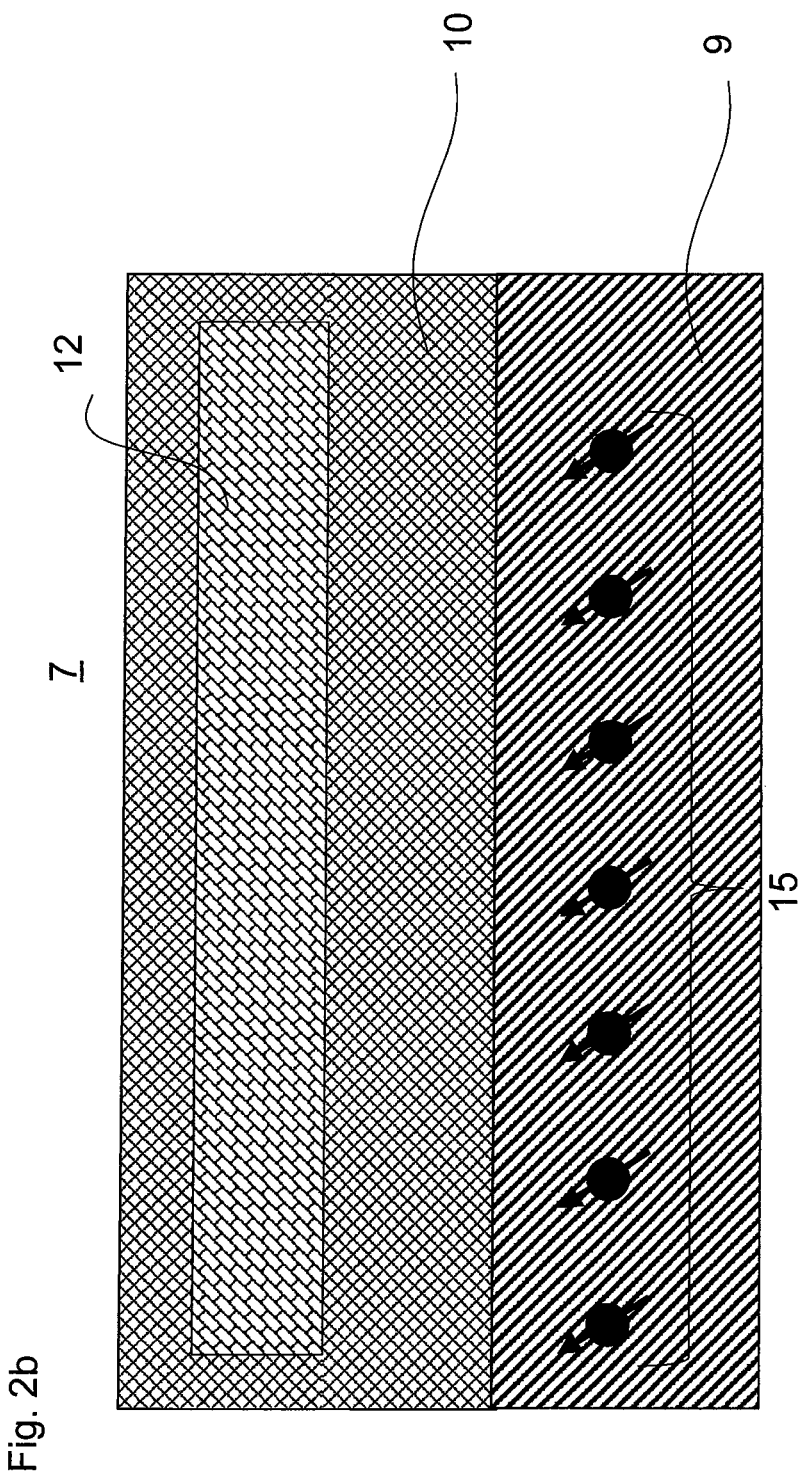

SENSOR COMPRISING A PIEZOMAGNETIC OR PIEZOELECTRIC ELEMENT ON A DIAMOND SUBSTRATE WITH A COLOUR CENTRE

CROSS REFERENCE TO RELATED APPLICATIONS

This application is the U.S. national phase of International Application No. PCT/EP2014/057788 filed on Apr. 16, 2014, and published in English on Oct. 22, 2015 as International Publication No. WO 2015/158383 A1, the contents of which are incorporated herein by reference.

FIELD OF THE INVENTION

The invention concerns a sensor comprising a first diamond substrate with at least one colour centre. The invention further concerns a method in which a change in a first piezomagnetic or piezoelectric primary element is detected.

BACKGROUND OF THE INVENTION

In a diamond, electron spins in a particular kind of colour centre, a nitrogen vacancy centre (NV centre), can be polarised and read out optically with the method of confocal fluorescence spectroscopy as demonstrated by A. Gruber et al. in "Scanning Confocal Optical Microscopy and Magnetic Resonance on Single Defect Centers", Science 276, 2012, 1997. Moreover, as F. Jelezko et al. show in "Observation of Coherent Oscillations in a Single Electron Spin", Phys. Rev. Lett. 92, 076401, 2004, such electron spins can be coherently manipulated with microwave fields.

M. D. Lukin et al. in "Nanoscale magnetic sensing with an individual electronic spin in diamond", Nature 455, 644-647, 2008 report the use of NV centres in diamond as magnetometer to measure externally applied DC/AC magnetic fields. In "Nanoscale imaging magnetometry with diamond spins under ambient conditions", Nature 455, 648-651, 2008, G. Balasubramanian et al. disclose a prototype nano-scale scanning probe with diamond spins, in which a nanocrystal containing a single NV centre is attached to the tip of a cantilever. G. Balasubramanian et al. report the imaging of the profile of the magnetic field produced by a nanometer-sized magnetic structure, with the spatial resolution about 20 nm. The method of optically detected magnetic resonance is used to measure the effect of a magnetic field on an NV centre electron spin.

In "A robust scanning diamond sensor for nanoscale imaging with single NV centres", Nature Nanotechnology 7, 320-324, 2012, A. Yacoby et al. position a single NV centre at the end of a high-purity diamond nanopillar, which they used as the tip of an atomic force microscope. A. Yacoby et al. report scanning a single NV centre within tens of nanometers from a sample surface, and imaging magnetic domains with widths of 25 nm by determining the sample magnetic field along the NV axis.

In "Stray-field imaging of magnetic vortices with a single diamond spin", Nature Commun. 4, 2279, 2013, V. Jacques et al. report the imaging of magnetic vortices in thin ferromagnetic films using NV magnetometry. V. Jacques et al. measure the three-dimensional distribution of stray magnetic fields above the magnetic nanostructures. The experiment is based on the same principle of NV-centre spin based magnetometry.

In "Nuclear magnetic resonance spectroscopy and imaging with single spin sensitivity" (submitted for publication), C. Müller et al. put a silicon layer on diamond surface, and use shallow implanted NV centers to detect $^{29}Si$ nuclei. In their experiment they find very high magnetic field sensitivity at the level of single $^{29}Si$ nuclear spins. C. Müller et al. create shallow NV centres (at the depth around 2 nm), and report their finding that these have good coherence properties for magnetic field sensing.

While the above works employed the principle of an NV centre magnetometer, none of the publications discloses the application of a colour-centre based diamond quantum sensor to detect the effect of pressure.

In "Electric-field sensing using single diamond spins", Nature Physics 7, 459-463, 2011, F. Dolde et al. report using a single NV defect centre spin in diamond to measure a three-dimensional electric-field which is produced by a microstructure with an applied voltage, acting on a diamond point defect spin sensor. F. Dolde et al. measure the magnetic transition frequency change of a NV centre due to an applied a. c. electric field. The underlying mechanism is based on the direct coupling between NV centre spin and the electric field, which puts limit on the achievable sensitivity. The achieved sensitivity for the measurement of electric field is 202 $(V\ cm^{-1})\ Hz^{-1/2}$.

In "Electronic properties and metrology of the diamond NV-centre under pressure", Phys. Rev. Lett. 112, 047601, 2014, Marcus W. Doherty et al. report the direct effect of pressure on the diamond on spin properties of NV centres in diamond. Marcus W. Doherty et al. measure the dependence of the resonance frequency of an NV centre ground spin in diamond on the pressure at room temperature, and find that the zero field splitting of the ground state triplet of an NV centre is approximately a linear function of pressure with the linear constant dD(P)/dP=14.58(6) MHz/GPa, which results in the sensitivity for the measurement of pressure on the order of 1 MPa $Hz^{-1/2}$. Marcus W. Doherty et al. also propose that the effect of pressure on the excited states of NV spin would be more prominent, and that the sensitivity for the measurement of pressure can reach the order of 0.1 kPa $Hz^{-1/2}$. However, ultra-low temperatures (<12 Kelvin) are necessary in order to have sufficiently narrow optical lines and long excite state lifetime, in order to achieve the reported measurement sensitivity. This prohibits the biological and medical applications as well as most everyday applications e.g. in electronic skin.

In "Nanometer-scale thermometry in a living cell", Nature 500, 54, 2013, M. D. Lukin et al. demonstrate nanoscale thermometry by measuring the change of the zero field splitting of the ground state triplet of an NV centre in nano diamond. M. D. Lukin et al. show the ability to measure the local thermal environment on length scales as short as 200 nm. Similar work is reported by David D. Awschalom et al. in "Fluorescence thermometry enhanced by the quantum coherence of single spins in diamond", Proc. Natl. Acad. Sci. U.S.A. 110, 8417-8421, 2013, and by J. Wrachtrup et al. in "High-Precision Nanoscale Temperature Sensing Using Single Defects in Diamond", Nano Lett. 13, 2738-2742, 2013. The idea underlying these works is based on the fact that temperature changes the zero field splitting of the ground triplet states with a coefficient dD(T)/dT=74 kHz/K. The achieved sensitivity for the measurement of temperature is 5-10 mk $Hz^{-1/2}$. A technique for the tracking, coherent manipulation, and readout out of an NV centre in cells was is disclosed in M. D. Lukin et al., Nature 500, 54, 2013, and in "Quantum measurement and orientation tracking of fluorescent nanodiamonds inside living cells" by L. P. McGuinness et al., Nature Nanotechnology 6, 358-363, 2011.

The common piezo-sensors suffer from the electrical noise that limits their sensitivity, and their size is usually beyond the scale of micrometer or millimeter. The techniques of optical tweezers, magnetic tweezers and atomic force microscopy (AFM) suffer from the same disadvantage that the probe size is large (micrometer-millimeter). Moreover, AFM suffers from the drawback that it is limited to interfaces. The large size of the probe limits the spatial resolution that can be achieved and prevents the application of the techniques on a nanometer scale system. In addition, optical tweezers, magnetic tweezers and atomic force microscopy cannot be highly integrated. What is more, atomic force microscopy does not operate at ambient conditions and optical tweezers require a free space solution.

PROBLEM TO BE SOLVED BY THE INVENTION

The invention aims to provide an improved sensor comprising a first diamond substrate with at least one colour centre. Moreover, the invention aims to provide a new method in which a change in a first piezomagnetic or piezoelectric primary element is detected.

SOLUTION ACCORDING TO THE INVENTION

The problem is solved by providing a sensor comprising a first diamond substrate with at least one colour centre, wherein the sensor further comprises a first piezomagnetic or piezoelectric primary element, which primary element is arranged to interact with the colour centre(s) of the first diamond substrate. In other words, a hybrid device of a diamond substrate and a piezomagnetic or piezoelectric element is provided. The diamond can be a synthetic diamond or a naturally occurring diamond. A colour centre in the context of the present invention is a localized defect in the diamond lattice which defect is filled by one or more electrons and can absorb and emit electromagnetic radiation.

The invention exploits the fact that a piezomagnetic or piezoelectric element can interact with a colour centre of a diamond such that a change in the piezomagnetic or piezoelectric element entails a corresponding change in the colour centre of the diamond. Accordingly, the problem is also solved by a method in which a change in the first piezomagnetic or piezoelectric primary element is detected by means of detecting a corresponding change in at least one colour centre of the first diamond substrate, which colour centre(s) interact with the first primary element.

In the context of the present invention, the term "first" expresses the fact that in some embodiments of the invention, in addition to the first diamond substrate or the first primary element there are further substrates or primary elements, respectively, as is discussed in more detail below. The expression "Primary element" indicates the fact that in some embodiments of the invention in addition to the one or more primary elements there are also one or more secondary elements, as is also discussed in more detail below.

In case the first primary element is piezomagnetic, the invention can exploit the fact that an external influence such as the exertion of a force on the piezomagnetic element or the temperature at the location of the piezomagnetic element affects the magnetisation of the piezomagnetic element's magnetic domains. This, in turn can affect, in particular via the element's stray magnetic field, the colour centre, in particular the energy levels of a ground state spin of the colour centre. Accordingly, in embodiments of the invention in which the primary element is piezomagnetic, the change in the primary element detected is a change of a magnetic property of the primary element.

Likewise, in case the primary element is piezoelectric, the invention can exploit the fact that an external influence such as the exertion of a force on the piezoelectric element or the temperature at the location of the piezoelectric element affects the charge distribution in the piezoelectric element. This, in turn can affect, in particular via the stray electric field, the colour centre, in particular the energy levels of a ground spin of the colour centre. Accordingly, in embodiments of the invention in which the primary element is a piezoelectric element, the change the primary element detected is a change of an electric property of the primary element.

It is an achievable advantage of the invention that the sensor in a straightforward manner can via the interaction between the primary element and the colour centre provided in the diamond substrate sense mechanical force, temperature or other parameters that affect the magnetic or electric properties of the primary piezomagnetic or piezoelectric element, respectively. In the context of the present invention, any reference to mechanical "force" is meant also comprise pressure, which is the force per unit area over which it is distributed.

PREFERRED EMBODIMENTS OF THE INVENTION

Preferred features of the invention which may be applied alone or in combination are discussed in the dependent claims.

The preferred first diamond substrate comprises several colour centres. Within the context of the present invention the terms "several" and "multiple" are used interchangeably in the meaning of "more than one". The first primary element can be arranged to interact with only one or with several colour centre(s) of the first diamond substrate. Preferably but not necessarily it is arranged to interact with all colour centres of the first diamond substrate. If the first primary element interacts with more than one colour centre, this can advantageously increase the sensitivity of the sensor. Moreover, a spatial resolution can be achieved corresponding to the spatial distribution of the colour centres as each colour centre predominantly is affected by the change in the part of the primary element or the primary element in the case of multiple primary elements that is nearest to the colour centre. The sensor's spatial resolution will be limited by the extent of the colour centre's electron wave function, which typically is around 1 nm. In other words, it is an achievable advantage of embodiments of the invention with several colour centres that changes at multiple positions of the primary element and/or at different primary elements in the case of multiple primary elements can be distinguished. The case of sensors with several primary elements is discussed in more detail further below.

In the typical embodiment of the invention, the several colour centres are arranged in a regular fashion, for example along one or several straight lines or in a two-dimensional array. In a typical regular arrangement, the colour centres are placed essentially equidistantly form each other in at least one direction. Preferably, the colour centres are distributed across an extended area, particularly preferably essentially within a common plane, in order to realize a spatial resolution across the extension of this area. Thereby, advantageously, a surface sensor can be obtained that measures the distribution of a physical parameter such as a force (including pressure), a temperature or an electric or magnetic field across a surface area.

To ensure that the interaction between the first primary element and the colour centre(s) is sufficiently strong, the colour centre(s) preferably is/are located at the distance of less than 20 nm (nanometers) from a surface, in the case of several colour centres preferably from the same surface, of the first diamond substrate. Moreover, in the case of several colour centres, these preferably are arranged in a common plane within the first diamond substrate, which plane preferably is in parallel to a surface of the first diamond substrate. The surface preferably is the surface directed towards or adjacent to the first primary substrate. Preferably, in the case of several colour centres, the colour centres have a preferential orientation. In this context, "preferential orientation" means that the orientations of each colour centre, defined as the vector connecting the nitrogen and the vacancy of a centre, are in parallel.

A preferred sensor according to the invention comprises several diamond substrates, each substrate comprising at least one colour centre. In this embodiment of the invention, the primary element may also interact with one or several, preferably all, colour centres of the further substrates of the sensor. In case the further substrates comprise several colour centres, these colour centres preferably in each of the further substrates are arranged as described above as a preferred arrangement in the first substrate.

The preferred diamond according to the invention is a synthetic diamond. A synthetic diamond suitable for the present invention can for example be produced by chemical vapour deposition (CVD), by detonation or by milling of larger crystals as is well known in the art. Synthetic diamonds can be enriched for $^{12}C$ to allow for a longer coherence time of colour centre spins. Furthermore, synthetic diamond material can be synthesized inexpensively in planar shape, including the deposition of diamond on the surface of other materials, e.g., by chemical vapour deposition (CVD).

While the present invention can be practiced using a diamond substrate with the natural abundance of carbon isotopes, a preferred diamond substrate is enriched for a $^{12}C$ isotope concentration above 99.9%, even more preferably above 99.99%. A suitable method for obtaining a synthetic diamond substrate of up to 30 mm in diameter with a $^{12}C$ isotopic enrichment of above 99.99% by means of microwave plasma-assisted chemical vapour deposition is described in Junichi Isoya et al., "Chemical Vapor Deposition of 12C Isotopically Enriched Polycrystalline Diamond", Jpn. J. Appl. Phys. 2012, vol. 51, pp. 090104. This publication's "Experimental Procedure" section spanning pages 1 and 2 is incorporated into the present disclosure by way of reference.

The preferred diamond substrate is a nano diamond, i.e. the substrate is smaller than 1000 nm in at least one spatial direction. A preferred diamond substrate is smaller than 1000 nm in two, even more preferably all three spatial dimensions. A particularly preferred nano diamond substrate is smaller than 400 nm in one, more preferably two, even more preferably all there spatial dimensions. An even more preferred nano diamond substrate is smaller than 100 nm in one, more preferably two, even more preferably all there spatial dimensions. Achievable advantages of this embodiment of the invention include that the size of the sensor can be reduced and that a nano-scale spatial resolution can be accomplished.

A preferred sensor may comprise not only one but several piezomagnetic or piezoelectric primary elements arranged to interact with the colour centre(s) of the diamond substrate(s). Each further primary element can, mutatis mutandis, have the properties and the arrangement described as advantageous herein with regard to the first primary element. In one embodiment, the several piezomagnetic or piezoelectric primary elements are arranged to interact with colour centre(s) of the same, typically but not necessarily of the only (i.e. the first), diamond substrate of the sensor. Alternatively, in the case of several substrates more than one, preferably all, of the several substrates may each be provided with one, or in some embodiments of the invention even several, primary piezomagnetic or piezoelectric element(s) arranged to interact with colour centre(s) of the respective substrate.

In the typical embodiment of the invention, the several primary elements are arranged in a regular fashion, for example along one or several straight lines or in a two-dimensional array. In a typical regular arrangement, the primary elements are placed essentially equidistantly from each other in at least one direction. Preferably, the primary elements are distributed across an extended area, particularly preferably essentially within a common plane, in order to realize a spatial resolution across the extension of this area. Thereby, advantageously, a surface sensor can be obtained that measures the distribution of a physical parameter such as a force (including pressure), a temperature or an electric or magnetic field across a surface area.

The preferred colour centre(s) is/are nitrogen vacancy centre(s), also referred to as NV centre(s). In an NV centre a nitrogen atom substitutes a carbon atom leading to a vacancy in the crystal lattice of the diamond. Other colour centres are suitable too, e.g. silicon vacancy centres where two neighbouring carbon atoms are missing and one silicon atom is occupying one or the other vacancy. Preferably, the change detected in the colour centre(s) is a change in an electron spin of the colour centre(s). Preferably, changes in the energies of the ground level of the colour centre(s)' electron spin(s) are measured. In a preferred method, for this purpose the electron spin is polarised by means of optical pumping. Preferably, the change in the colour centre(s) detected is a change in the colour centre(s)' fluorescence, for example by means of the method of Optically Detected Magnetic Resonance (ODMR) in the spin's ground state.

In a particularly preferred method according to the invention a microwave field is applied to the colour centre. Thereby it can advantageously be exploited that the electron spin of a suitable colour centre can be coherently manipulated with a microwave field. Preferably, the spin is prepared into a coherent superposition state of two ground spin-sublevels by means of the microwave field. It is achievable that as a result the ground spin-sublevels acquire a dynamical relative phase, which phase can for example be measured via a further microwave field followed by optical fluorescence of the colour centre spin. Alternatively, the coherent manipulation of the colour centre spin can be achieved by means of optical Raman fields at low temperatures, preferably below 10K in the case of NV centres, which couple the ground electronic spin states via an optically excited state. Preferably, the readout of the colour centre ground spin state is performed by the spin-dependent fluorescence measurement.

In a preferred embodiment of the invention, the piezomagnetic or piezoelectric primary element(s) is/are arranged to interact with the colour centre(s) of the substrate(s) magnetically or electrically. In other words, a magnetic or electric field generated by the primary element or a change in such electric or magnetic field influences the colour centre in a detectable manner. For this purpose preferably the piezomagnetic or piezoelectric primary element is in direct contact with the diamond substrate containing the colour centre(s) with which it interacts. The colour centre(s) preferably is/are not further than 20 nm away from the primary piezomagnetic or piezoelectric element(s) in order to insure a strong interaction.

In order to facilitate the interaction between the primary element and the colour centre(s), the primary element preferably is in direct contact with the diamond substrate. In an alternative embodiment of the invention, the primary element may be in indirect contact via a material that is permeable to an electric or a magnetic field between the primary element and the diamond substrate.

In some embodiments of the invention, the primary element or in the case of a sensor with several primary elements one or more of these several primary elements is/are piezomagnetic element(s) comprising, preferably consisting, of a solid ferrite material. A preferred solid ferrite is $Tb_{0.27}Dy_{0.73}Fe_2$ (Terfenol-D). Other piezomagnetic materials are also suitable. The preferred piezomagnetic material has a Curie temperature of above 300 K, more preferably of above 500 K, even more preferably of above 650 K. It is an achievable advantage of this embodiment of the invention that the sensor can operate at very high temperatures. Advantageously, nitrogen vacancy centres have good properties sufficient to enable the required sensing protocol even at high temperature. The sensor's operation temperature usually is limited by the Curie temperature.

Preferably, a bias magnetic field is applied to the piezomagnetic primary element(s) to tune the sensor to an optimal working regime. Preferably, the magnetic flux density of the bias magnetic field is smaller than 1 T, more preferably smaller than 0.1 T. The magnetic field is preferably aligned along the axis of the NV centres. Preferably, the field is provided by means of a permanent magnet or an electromagnet which does not rely on cooling.

In some embodiments of the invention the primary element or in the case of a sensor with several primary elements one or more of these several primary elements is/are piezoelectric element(s) comprising, preferably consisting of, a synthetic ceramic material. Preferred synthetic ceramics are $Pb[Zr_xTi_{1-x}]O_3$ (PZT), barium titanate ($BaTiO_3$), and materials from the group of piezoceramics, such as bismuth titanate $Bi_4Ti_3O_{12}$. Other piezoelectric materials are also suitable for this invention. Preferably, a bias electric field is applied to the piezoelectric primary element(s) to tune the sensor to an optimal working regime.

In the case that the sensor comprises several primary elements, it may comprise both piezomagnetic and piezoelectric primary elements, and in such a sensor preferably both a bias magnetic field and a bias electric field are applied. Alternatively, all elements comprise, preferably consist of, the same piezomagnetic or piezoelectric material.

In a preferred sensor, at least part of the, preferably the entire, first primary element extends as a layer across at least part of a surface, preferably the entire surface, of the first diamond substrate. The term "layer" is meant to indicate that the largest cross section of the surface of the first primary element which is directed towards the diamonds substrate is larger than the extension of the first primary element perpendicular to this surface. Likewise, the first diamond substrate preferably has the form of a layer. In the case of several primary piezomagnetic or piezoelectric elements and or several diamond substrates, preferably at least part, preferably the entirety, of each primary element extends as a layer across at least part, preferably the entirety, of each diamond substrate with which it interacts.

A preferred sensor in addition to the piezomagnetic or piezoelectric first primary element comprises a first secondary element which is arranged to interact with the first primary element. Again, "first" means that in some embodiment of the invention in addition to the first secondary element there are further secondary elements, as is discussed in more detail below. Preferably, the first primary element and the first secondary element interact mechanically in the sense that mechanical force, in the following also referred to as a strain, can be transferred between the primary and the secondary element. More preferably, a force exerted by the secondary element on the primary element or a change is such force influences the primary element in a way that changes the primary element's influence on the colour centre(s) in a detectable manner.

In order to facilitate the mechanical interaction between the secondary and the primary element, the secondary element preferably is in direct contact with the primary element. In an alternative embodiment of the invention, the elements may be in indirect contact via a material that mediates the transfer of force between the secondary and the primary elements.

The sensor may comprise several secondary elements, each arranged to interact with the primary element(s). Each further secondary element can, mutatis mutandis, have the properties and the arrangement described as advantageous herein with regard to the first secondary element. In one embodiment, the several secondary elements are arranged to interact with the same, typically but not necessarily the only (i.e. the first), primary element. Alternatively, in the case of several primary elements more than one, preferably all, of the several primary elements may each be provided with one or in some embodiments of the invention even several, secondary elements arranged to interact with the respective primary element.

In a preferred embodiment of the invention, the secondary element forms an island on the first primary element. In the case of several primary elements and/or several secondary elements, preferably each secondary element forms an island in or on the only (i.e. the first) primary element or, in the case of several primary elements in or on one of the several primary elements. The term "Island" means that in the secondary element is provided in a recess or an open or closed void of the primary element and fills the recess or the void partly or, more preferably, even completely. This arrangement facilitates the mechanical interaction between the secondary and the primary element.

In the typical embodiment of the invention, the several secondary elements are arranged in a regular fashion, for example along one or several straight lines or in a two-dimensional array. In a typical regular arrangement, the secondary elements are placed essentially equidistantly form each other in at least one direction. Preferably, the secondary elements are distributed across an extended area, particularly preferably essentially within a common plane, in order to realize a spatial resolution across the extension of this area. Thereby, advantageously, a surface sensor can be obtained that measures the distribution of a physical parameter such as a temperature or an electric field across a surface area.

A preferred secondary element(s) is/are piezoelectric. In this embodiment of the invention it can be exploited that the secondary element is sensitive to an electric field or a change in an electric field and that it changes its shape in response to the electric field or a change in the electric field. Through mechanical interaction with the primary element it can induce a change in the primary element, for example in the primary elements magnetic or electric properties. These, in turn can influence the colour centre(s) in the diamond substrate in a detectable manner as discussed above. The piezoelectric secondary element comprises, preferably consists of, a synthetic ceramic material. Preferred synthetic ceramics are $Pb[Zr_xTi_{1-x}]O_3$ (PZT), barium titanate ($BaTiO_3$), and materials from the group of piezoceramics, such as bismuth titanate $Bi_4Ti_3O_{12}$. Other piezoelectric materials are also suitable for this invention. Preferably, a bias electric field is applied to the piezoelectric primary element(s) to tune the sensor to an optimal working regime.

In a preferred embodiment of the invention, the secondary element(s) is/are thermally sensitive in the sense that the temperature or a change in the temperature through the interaction with the first element can induce a change in the first element. Preferably, the thermally sensitive element changes its shape in response to a change in the temperature at the location of the primary element. This, through mechanical interaction, can induce a change in the primary element. A preferred thermally sensitive island is composed of a material with a large thermal expansion coefficient and/or Young elastic modulus. Suitable materials include metals and metal alloys, such as aluminium, copper and steel. Other thermally sensitive materials are also suitable for this invention. In one preferred embodiment of the invention, the product of thermal expansion coefficient and Young elastic modulus (that determines the thermally induced force) is greater than 1.5 MPa $K^{-1}$, more preferably greater than 2 MPa $K^{-1}$, even more preferably greater than 2.5 MPa $K^{-1}$.

In the case that the sensor comprises several secondary elements, it may comprise both piezoelectric and thermally sensitive secondary elements, and in such a sensor preferably a bias electric field is applied. Alternatively, all elements comprise, preferably consist of, the same material, preferably piezoelectric or thermally sensitive.

The preferred sensor according to the invention has a diameter of less than 10 μm (micrometers), preferably less than 1 urn, more preferably less than 100 nm, for example between 10 and 100 nm. More preferably, the diameter is less than 30 nm, for example 10 nm. The diameter is measured in a plane parallel to the interface between the diamond substrate and the primary element. With this embodiment of the invention it can be exploited that the NV centre spins have good spin coherence properties on small scale, in particular in case of nano diamonds, i. e. diamonds that the diameter of the diamond substrate is less than 1 μm), which permits them to sense smallest electric and magnetic fields. Advantageously, with this embodiment of the invention pressure and other physical parameters can be measured with a nano-scale spatial resolution. The preferred sensor can be operating at the nano-scale such as inside living cells. Moreover, integrated sensing devices can be created.

In the case that the sensor comprises several colour centres for spatially resolved sensing, the sensor area preferably is greater than 0.1 mm² (square millimeters), more preferably greater than 1 mm², for example between 1 mm² and 100 mm². The sensor area is the area across which the sensor's colour centres are distributed.

In one preferred embodiment according to the invention, the sensor is coated with a non-toxic material, such as polymers with polyethylenimine (PEI) as one specific example. Advantageously, the coating yields a higher biocompatibility of the diamond and piezo elements layers in applications in vivo.

In a preferred method according to the invention, energies of the spin(s) of the colour centre(s), more preferably the ground spin sub-levels of the colour centre(s) are measured. The preferred colour centre(s) is/are NV centre(s). Preferably the colour centre(s)' spin-dependent fluorescence is measured, for example with optically detected magnetic resonance (ODMR) measurements, preferably by means of an intense laser.

More preferably, the spins are polarized by means of optical pumping, preferably with a laser. The spins preferably are measured with a pulse sensing scheme which is achieved by a microwave field. Preferably, in the pulsed sensing scheme, the ground spin sub-levels ms=−1 and +1 of the NV centre electrons are used. It is an achievable advantage of this method that the direct effect on the NV spin of the temperature instability and electric noise will shift the energies of these two spin sub-levels equally, and thus will not induce dephasing. This entails to a long coherence time of such a diamond spin sensor.

The preferred method according to invention is carried out at the temperature above 12 K. More preferably, the method is carried out at a temperature greater than 77 K, more preferably greater than 200 K, even more preferably greater than 273 K and most preferably at a temperature above 300 K. In this embodiment of the invention it can be exploited that cryogenic temperatures are not required to polarise the diamond substrate's electric spins.

The invention offers principles of hybrid sensors based on colour centres in diamond and piezo-active layers. With the invention a high sensitivity at various ambient conditions including room temperature conditions and atmospheric or high pressure conditions can be achieved. Moreover, with the invention nano-scale spatial resolution is achievable. Also, highly integrated devices can be obtained that operate stably even under adverse conditions.

In particular, the invention provides highly sensitive devices to measure weak pressure and force. The precision can go beyond sub-kPa $Hz^{-1/2}$ (for pressure measurement), sub pico-Newton (fN) $Hz^{-1/2}$ (for force measurement), sub-(V $cm^{-1}$) $Hz^{-1/2}$ (for electric field measurement), and sub-mk $Hz^{-1/2}$ (for temperature measurement). Sensors according to the invention with a nano-scale size can offer a spatial resolution better than 10 nm. Moreover, the integration of a basic pressure sensor unit can provide a device applicable for surface pressure collection with significantly enhanced sensitivity and response time, for example for interactive input control devices and for electronic skins.

BRIEF DESCRIPTION OF THE DRAWINGS

The invention is illustrated in greater details with the aid of schematic drawings:

FIG. 1a schematically shows in cross-sectional view the structure of (a) a force sensor according to the invention using a piezomagnetic primary element;

FIG. 1e schematically shows in cross-sectional view of hybrid sensors (i.e. the sensors of FIG. 1a to FIG. 1d) array, thereby obtaining a spatially resolved sensor.

FIG. 2a shows in cross-sectional view a spatially resolved force sensor according to the invention comprising a piezomagnetic primary element layer and a diamond layer that contains an array of colour centres;

FIG. 2b shows in cross-sectional view a spatially resolved electric field sensor according to the invention comprising a piezomagnetic primary element layer, a piezoelectric secondary element island and a diamond layer that contains an array of colour centres;

FIG. 6c shows the separation between two resonance frequencies in the ODMR spectra as a function of the pressure a;

DETAILED DESCRIPTION OF EMBODIMENTS OF THE INVENTION

Diamond Material

Figure 1B:
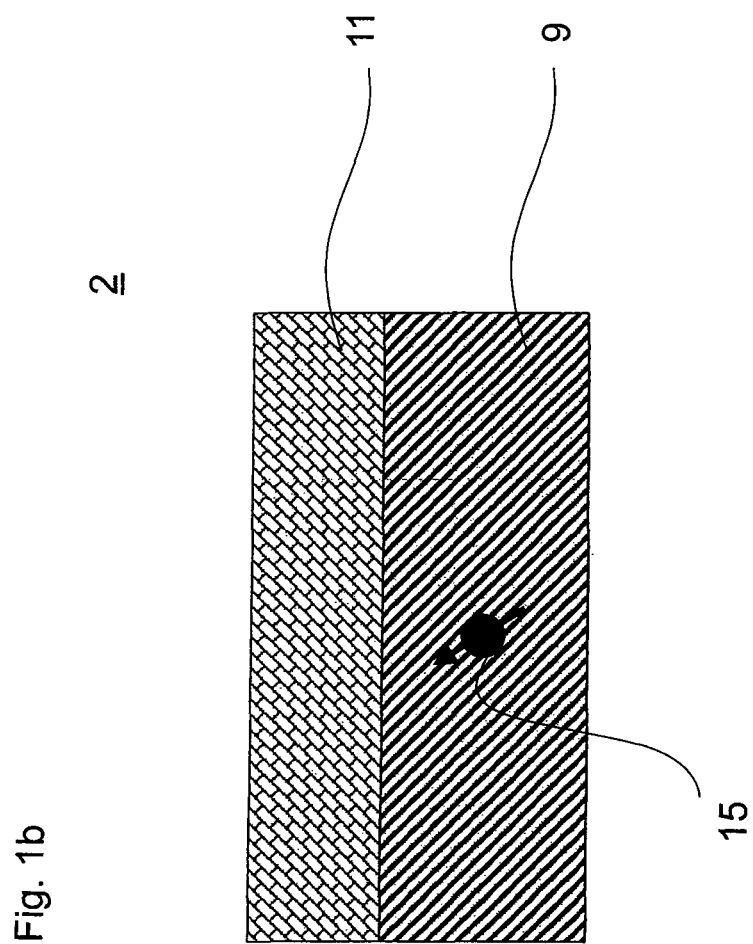
FIG. 1b schematically shows in cross-sectional view a force sensor according to the invention using a piezoelectric primary element.

Bulk diamond grown using high pressure high temperature (HPHT) method or chemical vapour deposition techniques as well as diamond nanocrystals can be employed for the invention. Doping of diamond with NV centres can be performed by electron irradiation of nitrogen containing diamond and implantation of nitrogen with subsequent annealing. Isotopic enrichment of diamond provides for a prolongation of the coherence time of NV centres but sensing experiments can also be performed in diamond crystals with different isotopic content (including natural abundance). A layer of NV centres at a controllable distance to the interface (with an depth uncertainty of 1-2 nm) in a synthetic diamond is created by nitrogen delta-doping, as described in David D. Awschalom et al. "Engineering shallow spins in diamond with nitrogen delta-doping", Appl. Phys. Lett. 2012, vol. 101, pp. 082413. The method is described in detail on page 1 and in the left column of page 2, which are incorporated into the present disclosure by way of reference. Note that the lateral positions of NV centres are not necessary to be in a regular lattice in order to gain the collective enhancement of measurement sensitivity.

Fabrication of Hybrid Diamond-Piezo Sensing Devices

Piezo-active thin films, i.e. piezomagnetic or piezoelectric thin films are deposited on the substrate of diamond with the methods of sputter deposition, such as radio frequency magnetron sputtering. The process is similar to the deposition of piezo-active thin films on other substrates, such Si and $LaAlO_3$. A suitable method of sputter deposition is disclosed by M. Ohring et al. in "Materials Science of Thin Films: Deposition and Structure", Academic Press, 2002. The method is described in detail in this paper's Chapter 5 (pages 205 to 230), which is incorporated into the present disclosure by way of reference.

Piezo-active thin films may also be grown on single-crystal diamond by means of chemical vapour deposition. A suitable method is similar to the method used to grow zinc oxide (ZnO) thin films on diamond surface to fabricate surface acoustic wave device, as disclosed by B. Zhao et al. in "Preparation and optimization of ZnO films on single-crystal diamond substrate by metal-organic chemical vapour deposition", Semicond. Sci. Technol. 19, 770, 2004. The method is described in detail in this paper's "Experiments" section (page 771), which is incorporated into the present disclosure by way of reference. However, in the method used for depositing a piezo-active film to manufacture a sensor according to the present invention, in the step of LP-MOCVD the precursors of diethyl zinc (DEZn) and $O_2$ for ZnO films are replaced by the ones for the specific piezo-active elements accordingly.

Piezoelectric and thermally active islands are fabricated by cutting thin films using, e.g., focused ion-beam patterning, photolithography, electron-beam lithography or other methods known to the skilled person. A suitable method of focused ion-beam patterning is disclosed by S. Bilhlmann et al. in "Size effect in mesoscopic epitaxial ferroelectric structures: Increase of piezoelectric response with decreasing feature size", Appl. Phys. Lett. 80, 3195, 2002. The method is described in detail in this paper's paragraph 3 (on page 3195), which is incorporated into the present disclosure by way of reference. A suitable photolithographic method is disclosed by K. Lee et al. in "Two-dimensional planar size effects in epitaxial PbTiO3 thin films", Appl. Phys. Lett. 85, 4711, 2004. The method is described in detail in this paper's Paragraphs 4-5 (on page 4711), which are incorporated into the present disclosure by way of reference. A suitable method of electron-beam lithography is disclosed by Chia-Wen Wu et al. in "Electron-beam lithography assisted patterning of surfactant-templated mesoporous thin films", Nanotechnology 15, 1886-1889 2004. The method is described in detail in this paper's "Experiments" section (pages 1887), which is incorporated into the present disclosure by way of reference.

Overview of the Experimental Setup

Figure 3:
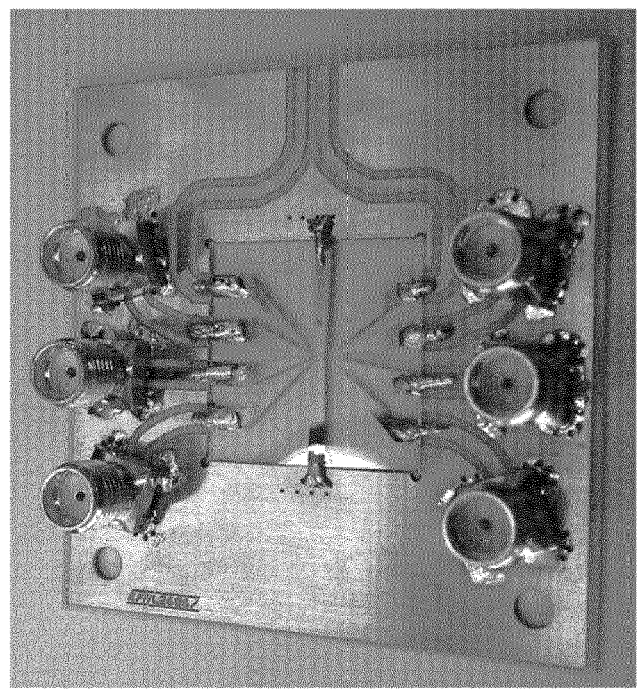
FIG. 3 shows on the left an optical microscope image of the microwave resonator structure on glass used in magnetic resonance experiments; On the right, an image of the holder with the strip structure is displayed.
Figure 3:
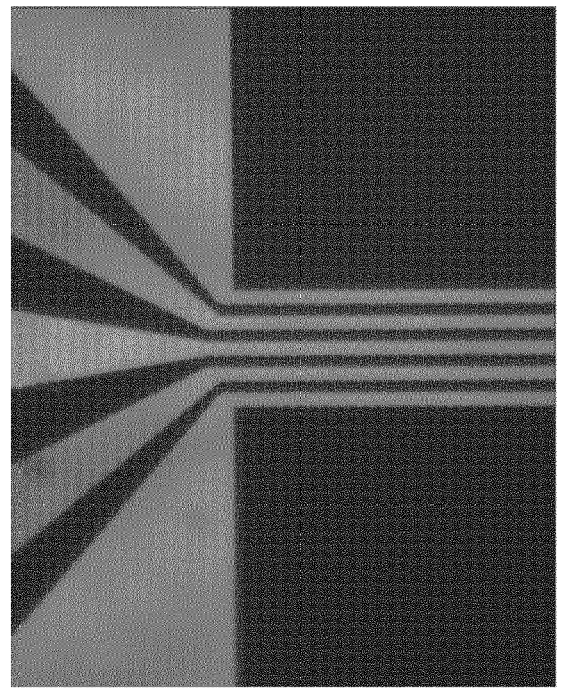
Figure 4A:
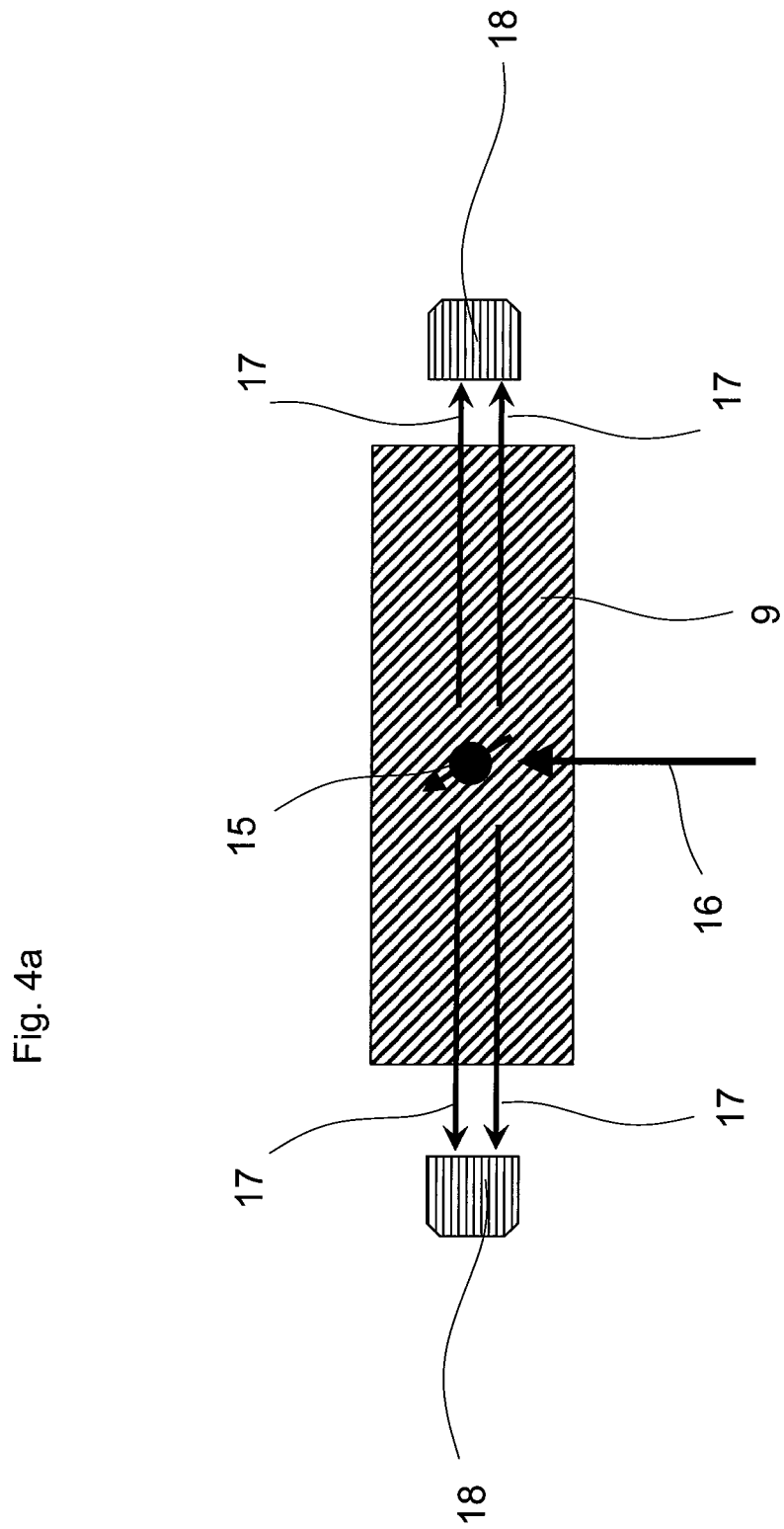
FIG. 4a shows a conceptual representation of an experimental setup for the optical pumping and optical detection of the electron spin of the NV centre.
Figure 4B:
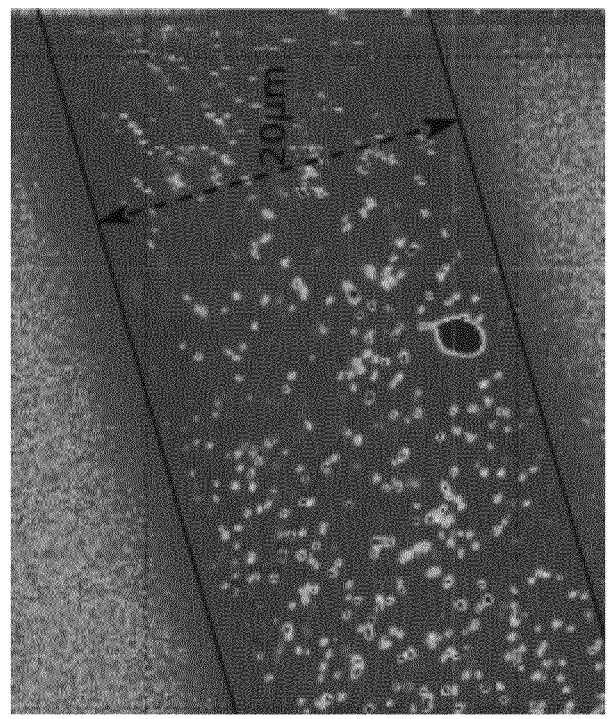
FIG. 4b shows a confocal map of single NV centres adjusted to a microwave strip line.
Figure 5:
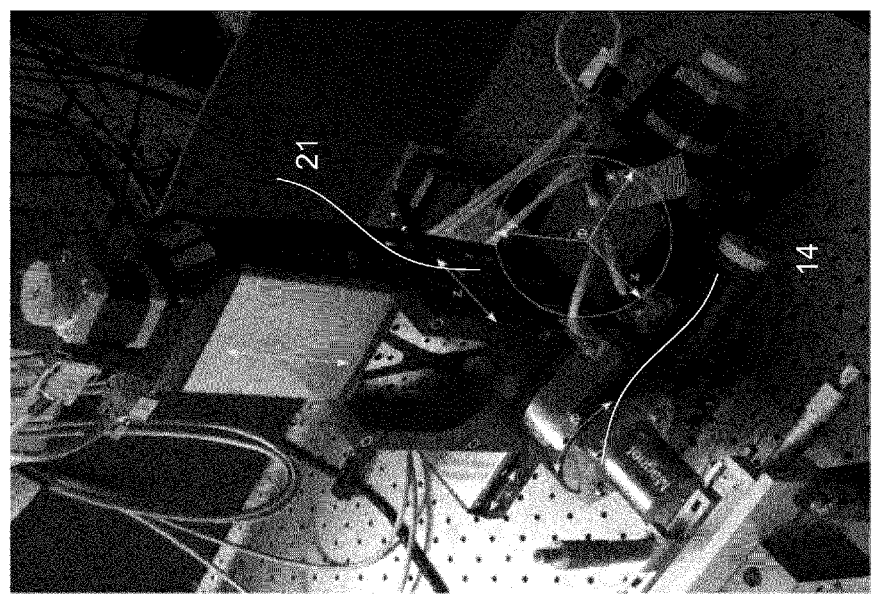
FIG. 5 shows a photograph of the magnet stage with a cylindrical magnet attached.

FIGS. 1a to 2c conceptually detail embodiments of sensors 1, 2, 3, 4, 5, 6, 7, 8 comprising a diamond substrate layer 9 and a piezomagnetic 10 or piezoelectric primary element layer 11, which in some embodiments is provided with a piezoelectric 12 or thermally sensitive secondary element island 13. The primary element layer is exposed to the magnetic field of a permanent magnet 14 as shown in FIG. 5. The diamond layer 9 contains a colour centre 15, which is an NV centre. A laser serves to polarize and read a colour centre's 15 spin. In order to move the diamond into the focus of the laser, the diamond or microscope objective lens is mounted on a piezo stage (not shown). The magnet 14 is mounted on rotation/translation stages of vector electromagnet (not shown) are used for alignment of the magnetic field with the crystallographic axis of the colour centre. FIG. 3 shows a microwave source used for the ODMR measurements and the coherent manipulation of the colour centre spin. The principle of the ODMR measurement is sketched in FIG. 4a. The colour centre 15 is exposed to (typically green) laser light 16 and the colour centre's 15 fluorescence light 17 is detected by means of photo detectors 18. A fluorescence image of a diamond substrate on top of the 4-strip microstructure is shown in FIG. 4b. On the top and the bottom of the image, one strip is displayed each. Between the strips, the diamond area can be seen. Bright spots correspond to the fluorescence emissions of NV centres.

Force Sensor Using Piezomagnetic Substrate

A sensor 1 according to the invention which can be used for measuring a force or pressure is shown in FIG. 1a. The device consists of a diamond substrate layer 9 with implanted NV centres 15 and a piezomagnetic element layer 10 directly adjacent and in contact to the diamond substrate layer 9. The response of the piezomagnetic layer 10, which has large magnetostriction, to a mechanical force or pressure leads to the change of the magnetization directions of magnetic domains of the piezoelectric material, and in turn to a change in the stray magnetic field that affects the energies of the ground spin levels of NV centres 15. A bias magnetic field is applied to piezomagnetic element layer 10 in order to render it more sensitive to pressure.

The spin-dependent fluorescence of the NV centre spins provides an efficient mechanism to perform optically detected magnetic resonance (ODMR) measurements in the ground state. The effect of pressure or force on the primary element layer, and thereby the value of force or pressure, is determined by the resonance frequencies in ODMR spectra. A suitable method of ODMR measurements of NV centre spin is described in A. Gruber et al. "Scanning Confocal Optical Microscopy and Magnetic Resonance on Single Defect Centers", Science 1997, vol. 276, pp. 2012 to 2014. The method is described in detail in this paper's paragraph 3 (on page 2013), which is incorporated into the present disclosure by way of reference.

An alternative method of using NV spin as a magnetometer to measure a magnetic field is a pulsed sensing scheme as describe in J. R. Maze et al. "Nanoscale magnetic sensing with an individual electronic spin in diamond", Nature 2008, vol. 455, pp. 644 to 647. The method is described in detail in this paper's FIG. 1 including the figure caption on page 645, the methods summary on page 647 and the publication's "Methods" supplement (lacking a page number), which are incorporated into the present disclosure by way of reference. The NV spin is first prepared into a coherent superposition state of two ground spin-sublevels by applying a microwave field. The energies of the ground spin-sublevels, which show dependence on the applied stress on the piezomagnetic layer, result in a dynamical phase and are measured via optical fluorescence of NV spin.

Force Sensor Using Piezoelectric Substrate

Another sensor 2 according to the invention which can be used for measuring a pressure or a force is shown in FIG. 1b. This device comprises piezoelectric element layer 11 directly adjacent and in contact to of the diamond substrate layer 9 with implanted NV centres 15. The response of the piezoelectric layer 11, which has a large piezoelectric constant, to a force or pressure leads to the change of the charge distribution within the piezoelectric material and in turn to a change in the stray electric field that affects the energies of the ground spin levels of NV centres as determined by ODMR scheme or pulsed magnetic sensing scheme. The value of force or pressure is thereby obtained from the stray electric field. The method relies on the measurement of stray electric field with a single NV spin sensor as described in F. Dolde et al. "Electric-field sensing using single diamond spins", Nature Physics 2011, vol. 7, pp. 459 to 463. The method is described in detail in this paper's FIGS. 1 and in 3 including the figure captions and in the methods section (pages 462), which are incorporate into the present disclosure by way of reference relevant portions of which are incorporated into the present disclosure by way of reference.

Electric Field Sensor

Figure 1C:
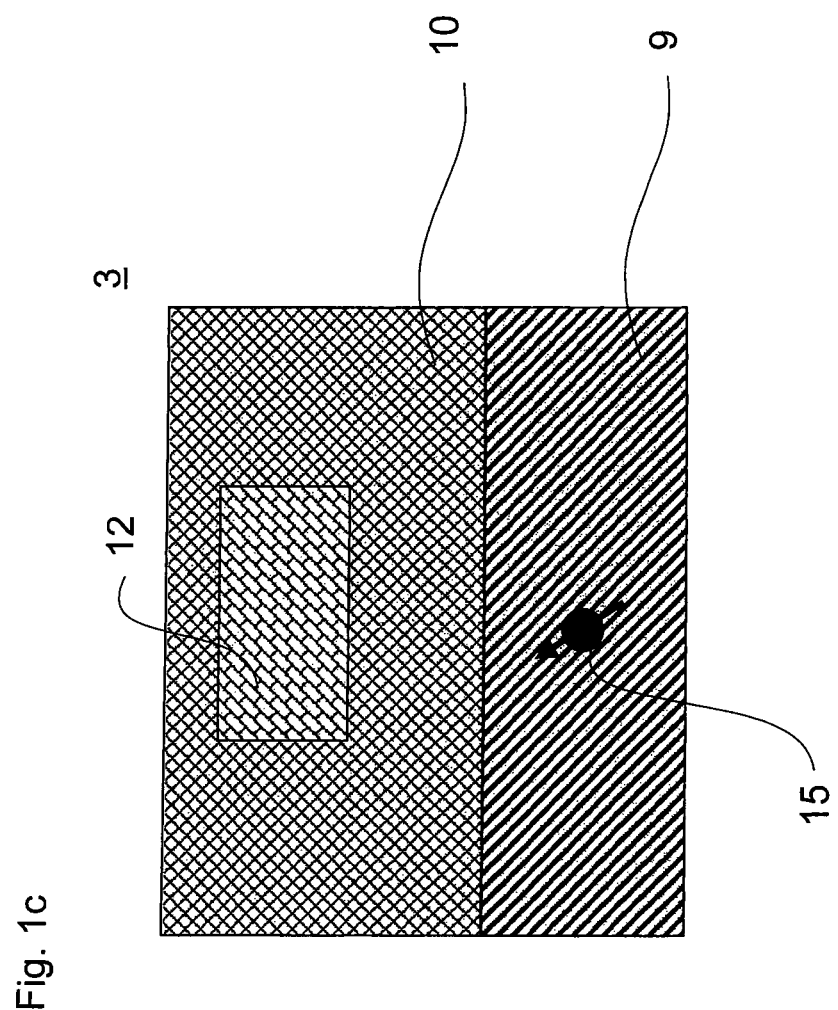
FIG. 1c schematically shows in cross-sectional view an electric field sensor according to the invention using a piezoelectric secondary element and a piezomagnetic primary element.

FIG. 1c shows a sensor 3 similar to the one in FIG. 1a but for the measurement of an electric field. For this, the sensor 3 comprises in addition to the piezomagnetic primary element layer 10 and a diamond substrate layer 9 containing NV centres 15 a piezoelectric secondary element island 12 provided in avoid of the primary element layer 10. An internal mechanical strain in the piezoelectric element island 12 is generated from an applied electrical field. The electric-field-induced strain generates a force which is transduced to the piezomagnetic element layer 10 generates a magnetic field, and is detected in the diamond substrate's 9 NV centres 15. The sensor 3 can be used for the sensing of a remote elementary charge (e.g. a single electron).

Temperature Sensor Using a Thermally Sensitive Island

Figure 1D:
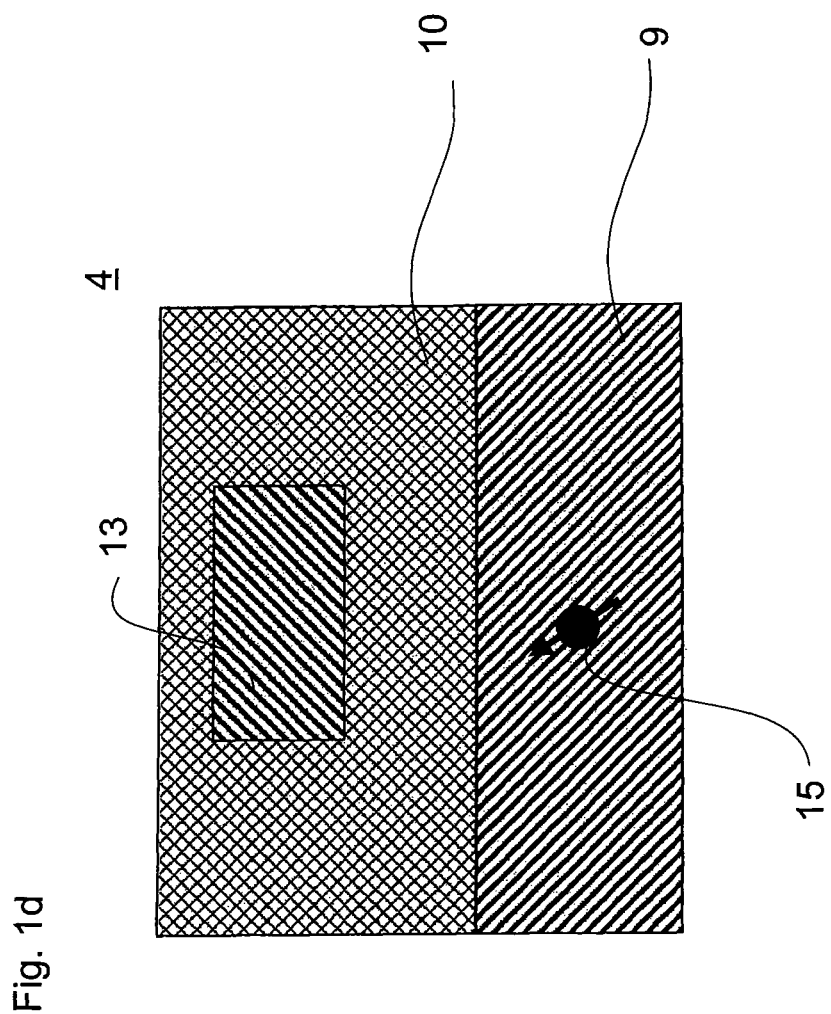
FIG. 1d schematically shows in cross-sectional view a temperature sensor according to the invention using a thermally sensitive secondary element and a piezomagnetic primary element.

FIG. 1d shows a sensor 4 for measuring the temperature. It comprises a thermally sensitive secondary element island 13, a piezomagnetic primary element layer 10 and a diamond substrate layer 9 containing NV centres 15. A change in temperature leads to the thermal expansion of thermal sensitive element island 13. The thermally induced strain generates a force which is transduced to the piezomagnetic element layer 10 generates a magnetic field, and is detected in the diamond substrate's 9 NV centres 15. This can solve the problem, according to the invention, of providing a sensitive transducer for various physical parameters, such as magnetic field, electric field, pressure (force) and temperature. Possible applications of temperature sensing include, the observation of chemical reactions at the nanoscale, or the observation of temperature inside cells to monitor biological processes at the nanoscale.

Spatially Resolved Force Sensor

FIG. 2a shows a spatially resolved force sensor 6 according to the invention comprising a diamond substrate 9 with a two-dimensional array of NV centres 15, a piezomagnetic primary element layer 10 and a diamond layer containing an array of colour centres 15. With this sensor 6, a force or pressure distribution on the surface of the sensor can be measured.

Spatially Resolved Electric Field Sensor

FIG. 2b shows a spatially resolved electric field sensor 7 according to the invention comprising a diamond substrate layer 9 with a two-dimensional array of NV centres 15, a piezomagnetic primary element layer 10, a piezoelectric secondary element island 12, the diamond layer 9 containing an array of colour centres.

Spatially Resolved Temperature Sensor

Figure 2C:
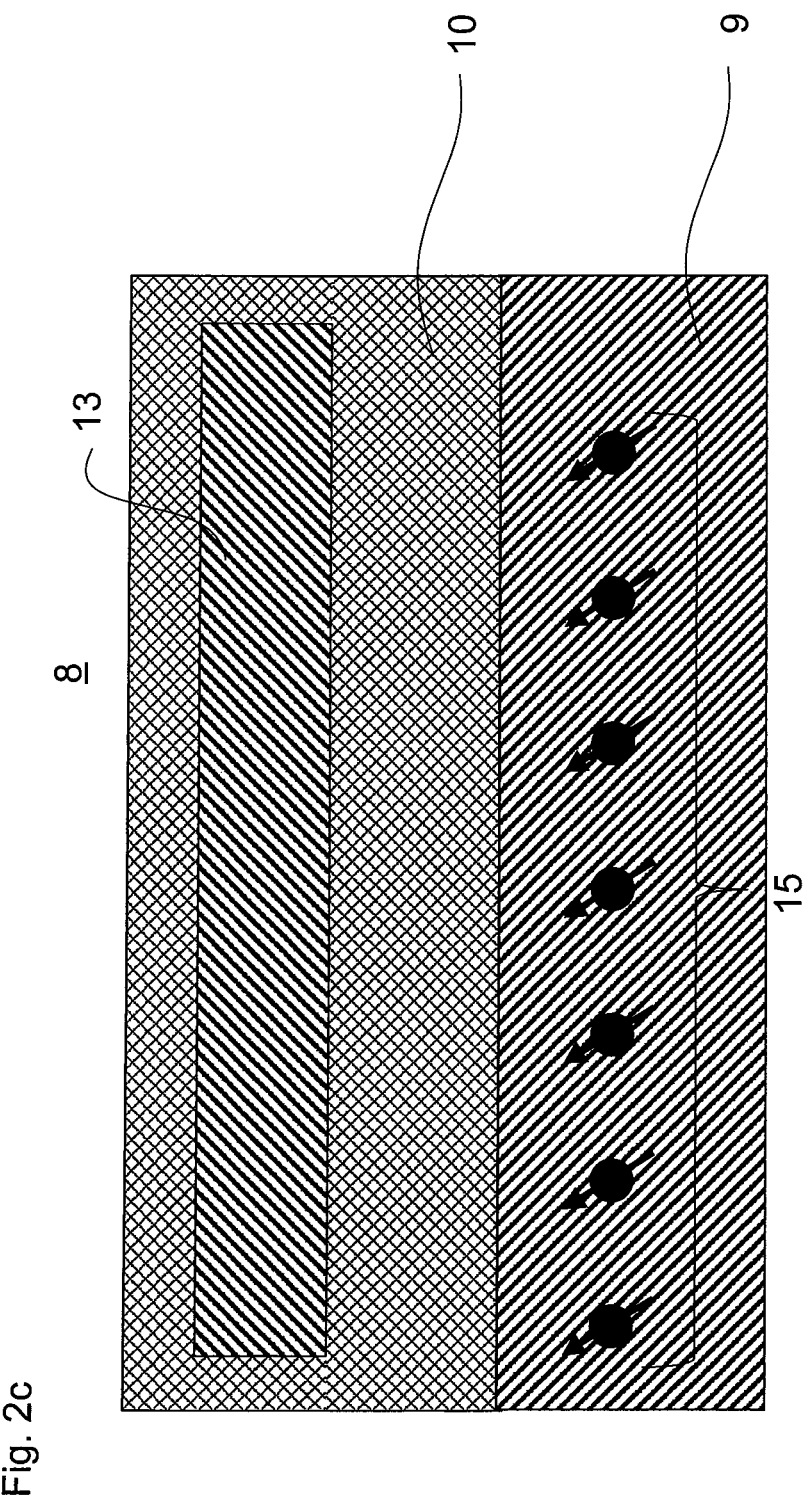
FIG. 2c shows in cross-sectional view a spatially resolved temperature sensor according to the invention comprising a primary element layer adjacent to the diamond substrate, a thermally sensitive secondary element island and a diamond layer that contains an array of colour centers.

FIG. 2c shows in cross-sectional view a spatially resolved temperature sensor 8 according to the invention comprising a diamond substrate layer 9 with a two-dimensional array of NV centres 15, a primary element layer 10 adjacent to the diamond layer 9, and a thermally sensitive secondary element island 13 the diamond layer 9 containing an array of colour centres.

A layer of NV centres in a synthetic diamond is created with nitrogen delta-doping, as described in David D. Awschalom et al. "Engineering shallow spins in diamond with nitrogen delta-doping", Appl. Phys. Lett. 2012, vol. 101, pp. 082413. A diamond with a lateral surface area above 1 mm$^2$, in which the NV spins (with the number on the order of $10^9$) in the entire diamond increases the sensitivity for the overall pressure measurement by at least a factor of $10^4$.

Sensor Arrays

The sensors 1, 2, 3, 4 of FIGS. 1a to 1d can be combined into arrays, thereby obtaining a spatially resolved sensor array 19. For example, by combining the sensors 1, 2 of FIG. 1a or 1b, a surface pressure collector can be created. When combining the sensor 1, 2, 3, 4 into a sensor array, each individual sensor can have its own substrate 9, primary element layer 10, 11 and possibly secondary element islands 12, 13 (FIG. 1e). To physically combine them into an array, they a mounted on a common substrate 20; suitable substrates are known to the skilled person.

It is an achievable advantage of the spatially resolved sensors 6, 7, 8 and the sensor array 19 discussed above that they are scalable, i.e. that in principle an unlimited number of sensing units (In the case of FIGS. 2a to 2c) or sensors 1, 2, 3, 4 (in the case of FIG. 1) can be combined with each other. This can solve the problem of integration of pressure sensors towards applications such as tactile imaging, electronic skin, and interactive input/control devices. Such surface pressure collector can be used to detect acoustic and vibrational motion, detect the Casimir effect where minute forces have to be measured at smallest distances (below 100 nm), and to study fundamental quantum physics phenomena.

Detection Scheme Based on Optically Detected Magnetic Resonance (ODMR)

In the present embodiments, single NV centres are detected using a confocal microscopy technique. A laser beam diode pumped solid state laser operating at 532 nm is focussed onto a diffraction limited spot using a high numerical aperture microscope objective (Olympus UPLAPO 60×). The sample is scanned using a piezo driven stage (nPoint, Inc.). Fluorescence is collected by the same microscope objective and focussed on avalanche photodiodes with single photon sensitivity (SPCM-AQRH, Excelitas). By observation of photon-antibunching, it can be detected that an individual NV centre is in focus. Fluorescence detection of magnetic resonance on single electron spin is based on optical contrast of spin states associated with NV centres. The method of side-collection spin-dependent photoluminescence as developed in D. Le Sage et al. "Efficient photon detection from colour centres in a diamond optical waveguide", Phys. Rev. B 85, 121202(R) (2012), is used for improve the optical detection efficiency. The method is described in detail on pages 1 and 2 of the publication, which are incorporated into the present disclosure by way of reference.

Initialization of NV Centre Electron Spin

Electron spins associated with NV centres are polarised by the application of a short (300 ns) laser 4 pulse. Optical pumping is achieved by excitation of the NV centre into an excited electronic state. The decay of this state occurs predominantly into one of the spin sublevels of the ground state.

Microwave Excitation for Coherent Manipulation of NV Centre Electron Spin

In order to excite microwave transitions of single colour centres in diamond, the sample is placed on a home built microwave strip line providing efficient excitation of the diamond. At the top in FIG. 3, an optical microscopic picture of the structure is shown, which is fabricated on a glass cover slip by conventional photolithography and is used in the magnetic resonance experiments. The width and gap of each microstrip is 20 μm. At the bottom in FIG. 3, a picture of the holder with the strip line can be seen. The signal is applied via coaxial cables connected to SMA connectors and matched to the two coplanar microstrips.

A commercial microwave source (Anritsu MG 37020A) is used in the experiments. In order to achieve Rabi frequencies of a few MHz, the source is amplified using a commercial high power microwave amplifier (10 W, Gigatronics GT 1000A). Phase control of microwave fields is achieved using commercially available phase shifters (Narda, Inc.). Microwave pulses are formed using commercial microwave switches (General Microwave, F9914). The strength of the microwave drive is controlled by the output level of the microwave source.

Time Resolved Measurements

Optical pulses for optical spin polarisation and time resolved detection of magnetic resonance are produced using acousto-optical modulators (Crystal Technology). Microwave, optical pulses, sample scanning and data acquisition is synchronised by a computer controlled pulse generator (Tektronix, DTG) connected to drivers of acousto-optical modulators, microwave switches and a fast photon counter (FastComtec, P7998).

The optical detection of magnetic resonance is carried out in accordance with the scientific publications Jelezko, F. et al., "Single defect centres in diamond: A review." Physica Status Solidi (a) Applications and Materials Science, 2006. 203(13): pages 3207 to 3225, Jelezko, F. et al., "Read-out of single spins by optical spectroscopy.", Journal of Physics-Condensed Matter, 2004. 16(30): pages R1089 to R1104 and Jelezko, F., et al., "Observation of coherent oscillations in a single electron spin", Physical Review Letters, 2004. 92(7), the relevant portions of which are incorporated into the present disclosure by way of reference.

Magnetic Field Control

A magnetic field on the order of up to 1 T is generated by a permanent magnet 14 (magnets4you GmbH) located about 100 μm from the diamond face. In order to align the magnetic field with the crystallographic axis (z-axis) of the NV defect, the magnet is moved using rotation and translation stages 21 (Micos GmbH) as shown in FIG. 5.

Sensing of Pressure Response of the Piezo Elements Layers

Figure 6A:
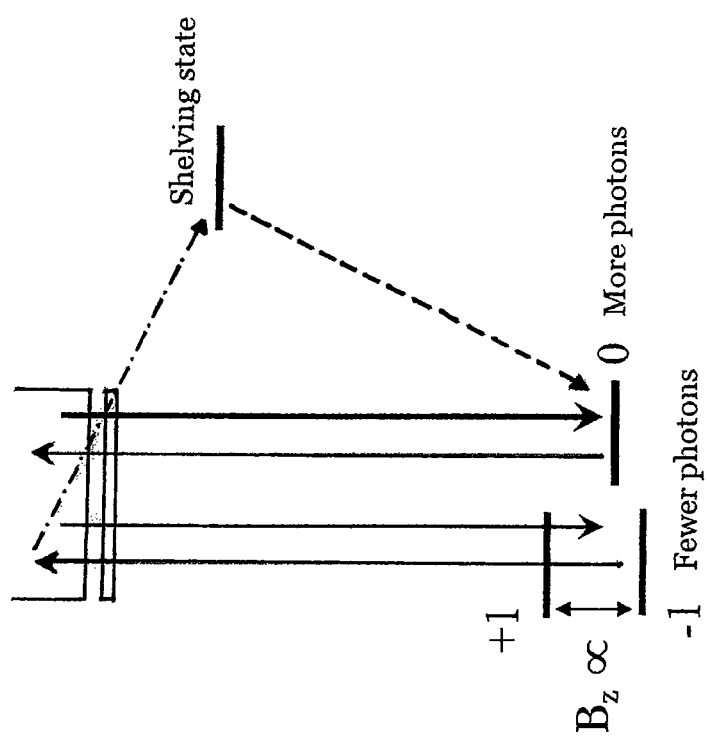
FIG. 6a illustrates the ground spin level structure of a single NV centre, which is a spin triplet ($|1\rangle$, $|0\rangle$, and $|-1\rangle$), with a 2.87 GHz crystal field splitting. A Zeeman shift gives rise to the splitting of $|1\rangle$ and $|-1\rangle$. By applying an excitation (green) light with a wavelength of about 530 nm, the NV centre exhibits spin-dependent photo-luminescence near the zero phonon line at the wavelength about 638 nm even at room temperature. This allows for optical pumping and optical detection of the NV centre spin state.

The ground $^3A_2$ level of the NV spin exhibits a zero field splitting of D=2.87 GHz between the $m_s=0$ and $m_s=\pm 1$ spin sub-levels. The ground spin level structure is illustrated in FIG. 6a. The spin Hamiltonian, including the Zeeman interaction with an external magnetic field, and the coupling with an external electric field, is given by $$H=(D+d_{gs}^{\parallel}E_z)[S_z^2-\tfrac{1}{3}S(S+1)]-d_{gs}^{\perp}[E_x(S_xS_y+S_yS_x)+E_y(S_x^2-S_y^2)]+\gamma(B_xS_x+B_yS_y+B_zS_z), \quad (1)$$

where γ is the electron gyromagnetic ratio, $B_{x,y,z}$ and $E_{x,y,z}$ represent the three components of the magnetic field and the electric field, which arise from both the applied external magnetic/electric field and the stray magnetic/electric field generated by the piezomagnetic film. The effect of the strain on the NV centre, as quantified by E, induces ground state spin sub-level mixing and is usually much smaller (on the order of MHz) than the energy splitting along the NV axis.

The resonance frequencies $\omega_{\pm 1}$ in the optically detected magnetic resonance (ODMR) measurements spectra correspond to the electronic transitions from the spin sub-level $m_s=0$ and $m_s=\pm 1$ respectively, which depend on the magnetic field acting on the NV centre. FIG. 6c shows one example of the response of the ODMR resonance spectra of the NV spin under a weak pressure (sub-MPa). The separation A between two resonance frequencies in the ODMR spectra as a function of the stress a is shown. The value of Δ is 15.55 GHz for σ=0. The dimension of the Terfenol-D film is chosen as $(15\ nm)^3$, and the distance from the NV centre to the interface is d=15 nm. The applied external magnetic field is $B_0=2350$ G along the ⟨001⟩ direction, and the stress is along the ⟨111⟩ direction. The temperature is 300K.

Figure 6B:
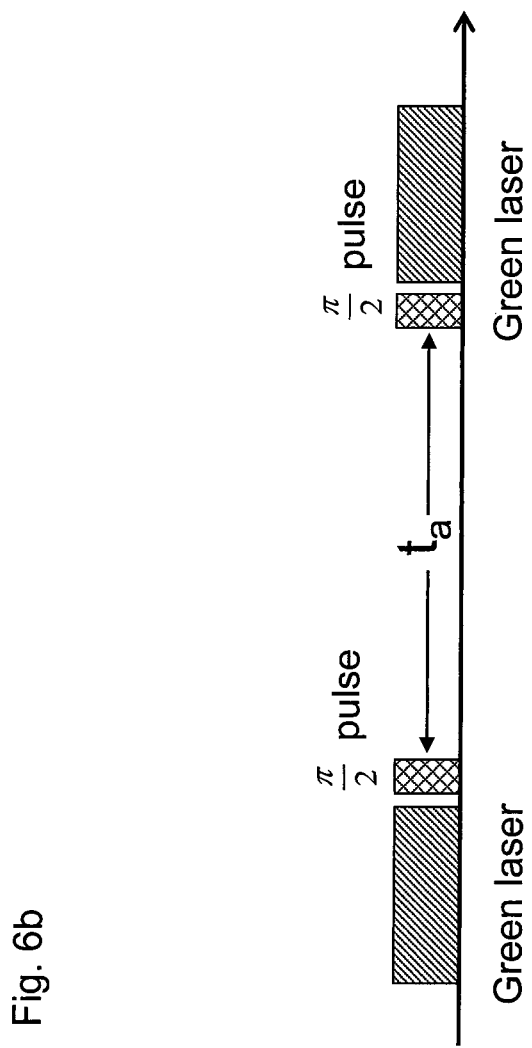
FIG. 6b shows the pulse sequence that is used to measure the response of single NV centres to the external parameters, such as pressure, magnetic field, electric field, and temperature. The NV centre spin is initialized by optical pumping with a green laser; which is further prepared into a coherent superposition of $|1\rangle$ and $|-1\rangle$ with microwave field manipulation. After a free evolution time t, the phase information resulting from external signals is mapped back to spin state population with microwave field manipulation, which is then readout by optical detection with a green laser.
Figure 6C:
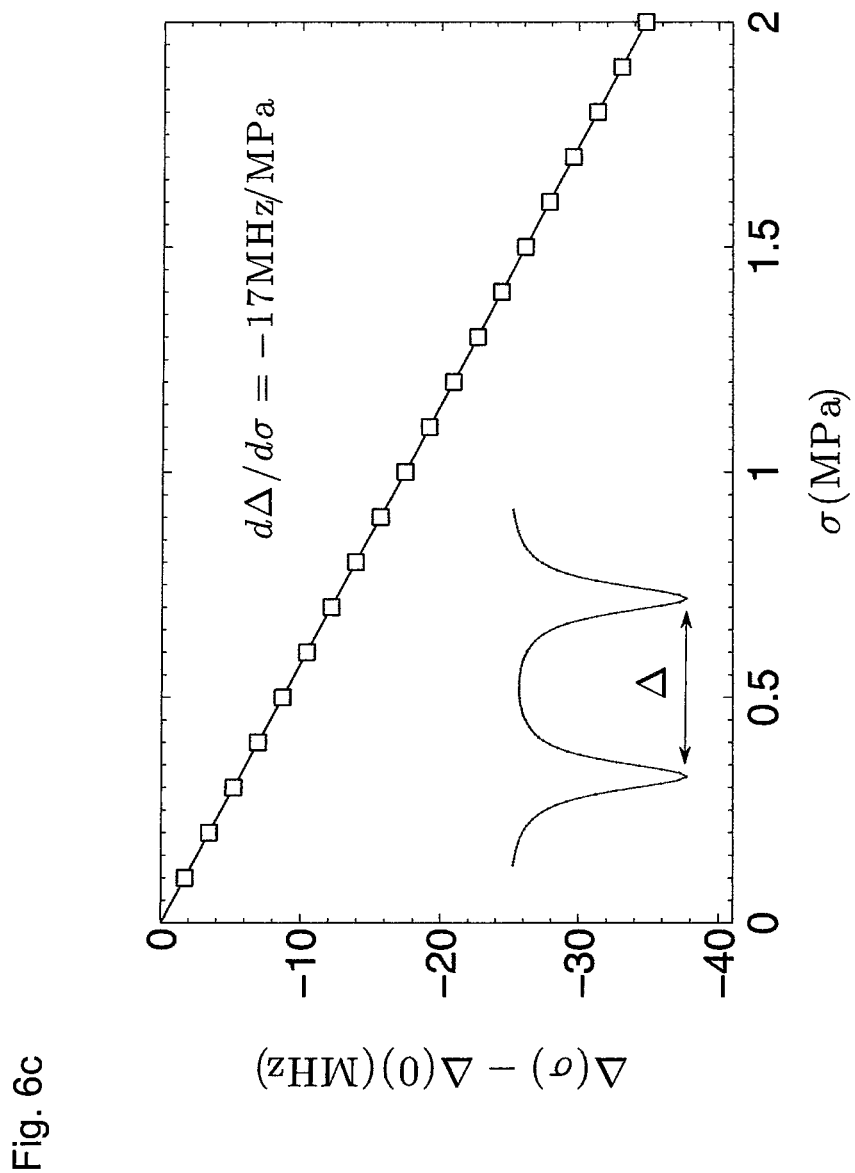
Figure 6D:
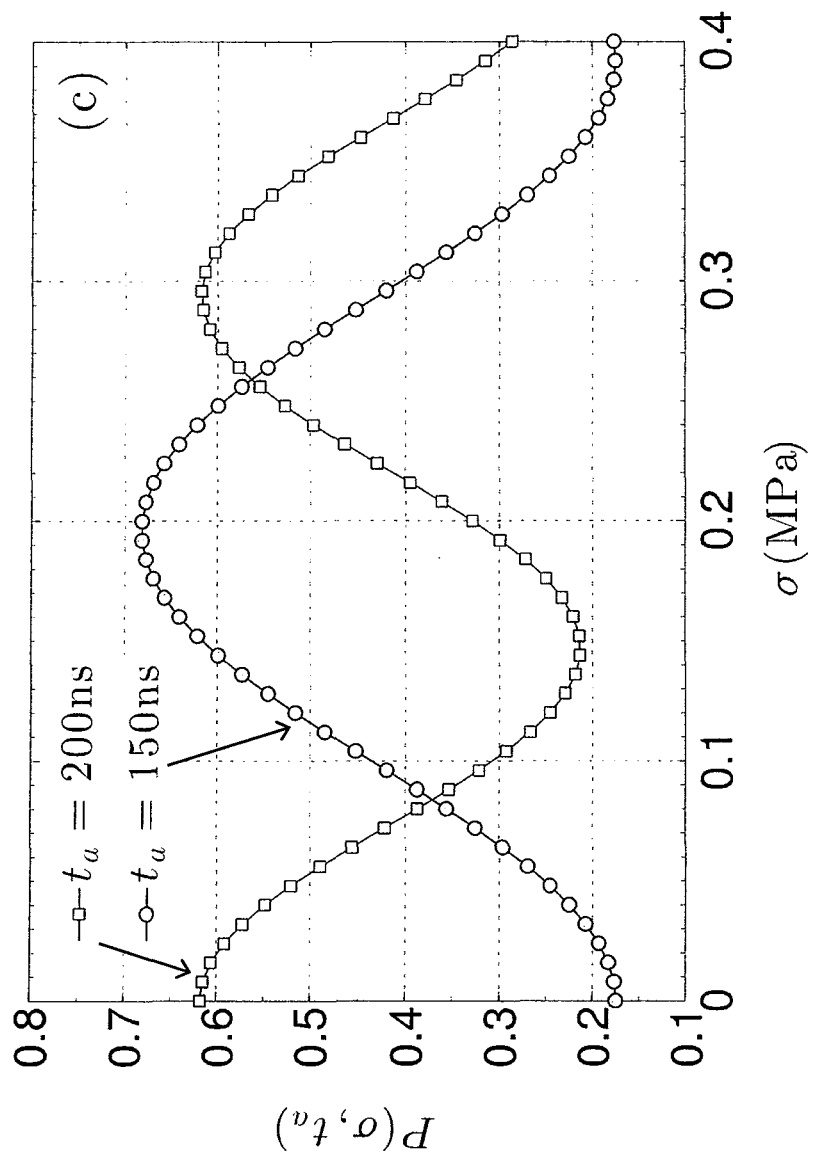
FIG. 6d shows the signal as a function of the applied uniaxial stress a at the acquisition time ta.

In the pulse-sensing scheme, an example of which is illustrated in FIG. 6b, the nitrogen-centre electronic spin is first prepared into a coherent superposition state $|\Phi\rangle = \sqrt{1/2}(|-1\rangle+|+1\rangle)$ by applying a microwave field $H_d=\Omega[\cos(\omega_{+1}t)|+1\rangle\langle 0|+\cos(\omega_{-1}t)|-1\rangle\langle 0|]+h.c.$ for a duration $t_{\pi/2}=\pi/\Omega$. The ideal evolution of the NV centre spin is $|\Phi\rangle = \frac{1}{2}(|-1\rangle+e^{-it\Delta}|+1\rangle)$, where Δ is the frequency difference of the resonance in ODMR spectra. For the NV centre spin in isotopically engineered diamond, the magnetic noise from the $^{13}C$ nuclear spin bath is negligible, and the dominant magnetic noise in the present model arises from the fluctuation in the piezo element layers.

The real dynamics of the NV centre spin under the environmental noise is described by the master equation as follows $$\frac{d}{dt}\rho = -i[H,\rho] + \Gamma_z(0)\Lambda(\rho,s_z) + \sum_{k=\pm 1}\Gamma_\perp(\omega_k)\Lambda(\rho,s_{0k}) \quad (2)$$

where $\Gamma_\perp(\omega_k)$ and $\Gamma_z(0)$ represent the power spectra of the magnetic noise parallel and perpendicular to the NV axis, $\Lambda(\rho,s_z)=s_z\rho s_z-\rho$ with $s_z=|+1\rangle\langle+1|-|-1\rangle\langle-1|$, and $\Lambda(\rho,s_{0k})=L(\rho,|k\rangle\langle 0|)+L(\rho,|0\rangle\langle k|)$ with $L(\rho,A)=A\rho A^\dagger - \frac{1}{2}(A^\dagger A\rho+\rho A^\dagger A)$. The spin state of the NV center after a free evolution time t is given by the solution of the master equation in Eq. (2):

$$\rho(t) = \begin{pmatrix} p_{-1} & 0 & q \\ 0 & p_0 & 0 \\ q^* & 0 & \frac{1}{2} \end{pmatrix} \quad (3)$$

where $$p_{-1} = \frac{1}{4}[1+e^{-t\Gamma_\perp(\omega_{-1})}],$$

$$p_0 = \frac{1}{4}[1-e^{-t\Gamma_\perp(\omega_{-1})}],$$

and $$q = \frac{1}{2}e^{-\frac{t}{2}\Gamma_\perp(\omega_{-1})}e^{-4t\Gamma_z(0)}e^{-it\Delta}.$$

The fluorescence measurement after the acquisition time t measures the state $m_s=0$ population is as follows:

$$P(\sigma,t) = \frac{1}{8}[3+e^{-t\Gamma_\perp(\omega_{-1})}] + \frac{1}{2}\cos(\Delta t)e^{-t\Gamma_\perp(\omega_{-1})}e^{-4t\Gamma_z(0)} \quad (4)$$

By choosing a larger acquisition time of t, it is possible to improve the sensitivity, while the spin will suffer more from the magnetic noise. The sensitivity for pressure measurement can achieve $n_\sigma \sim 0.35$ kPa $Hz^{-1/2}$ with a layer area ~200 $nm^2$, which corresponding to a force measurement sensitivity $n_F$ of ~75 femto-Newton (fN) $Hz^{-1/2}$. The optimal choice of t is on the order of the coherence time of the NV centre spin. The sensitivity may be further improved by optimizing the dimension of the hybrid system, and using an array of NV centres.

Sensing of Electric Field with Colour Centres in Diamond and Piezo Element

In a method of the invention, a hybrid device that consists of a synthetic diamond layer formed by chemical vapour deposition (CVD) doped with NV centres during growth, a piezomagnetic element layer, and a piezoelectric element island on a substrate, measures electric field. An electric field induces a stain e of the piezoelectric element island, which generates a stress σ=ε·Y acting on the attached piezomagnetic layer with Y denotes the Young's modules of the piezoelectric material. For a piezoelectric island which has large piezoelectric constants, such as $Pb[Zr_xTi_{1-x}]O_3$ (PZT), the electric-field-induced strain can be as large as $\varepsilon_e=0.0002$ $(MV/m)^{-1}$, the corresponding Young's modules is $Y\sim 10^5$ MPa. The sensitivity for the measurement of electric field thus reaches $$\eta_E = \eta_\sigma/(\varepsilon_e \cdot Y) \quad (5)$$

The sensitivity for the measurement of pressure of $\eta_\sigma \sim 0.35$ kPa $Hz^{-1/2}$ implies the sensitivity for the measurement of electric field $\eta_E \sim 0.2$ (V $cm^{-1}$) $Hz^{-1/2}$, which represents three orders of magnitudes of improvement over the result reported by F. Dolde et al. in "Electric-field sensing using single diamond spins", Nature Physics 2011, vol. 7, pp. 459-463. This sensitivity would allow for the detection of the electric field produced by a single elementary charge at a distance from the NV-spin sensor of ~8 μm in around is, and thus opens the possibility of remote sensing of a single charge.

Figure 6E:
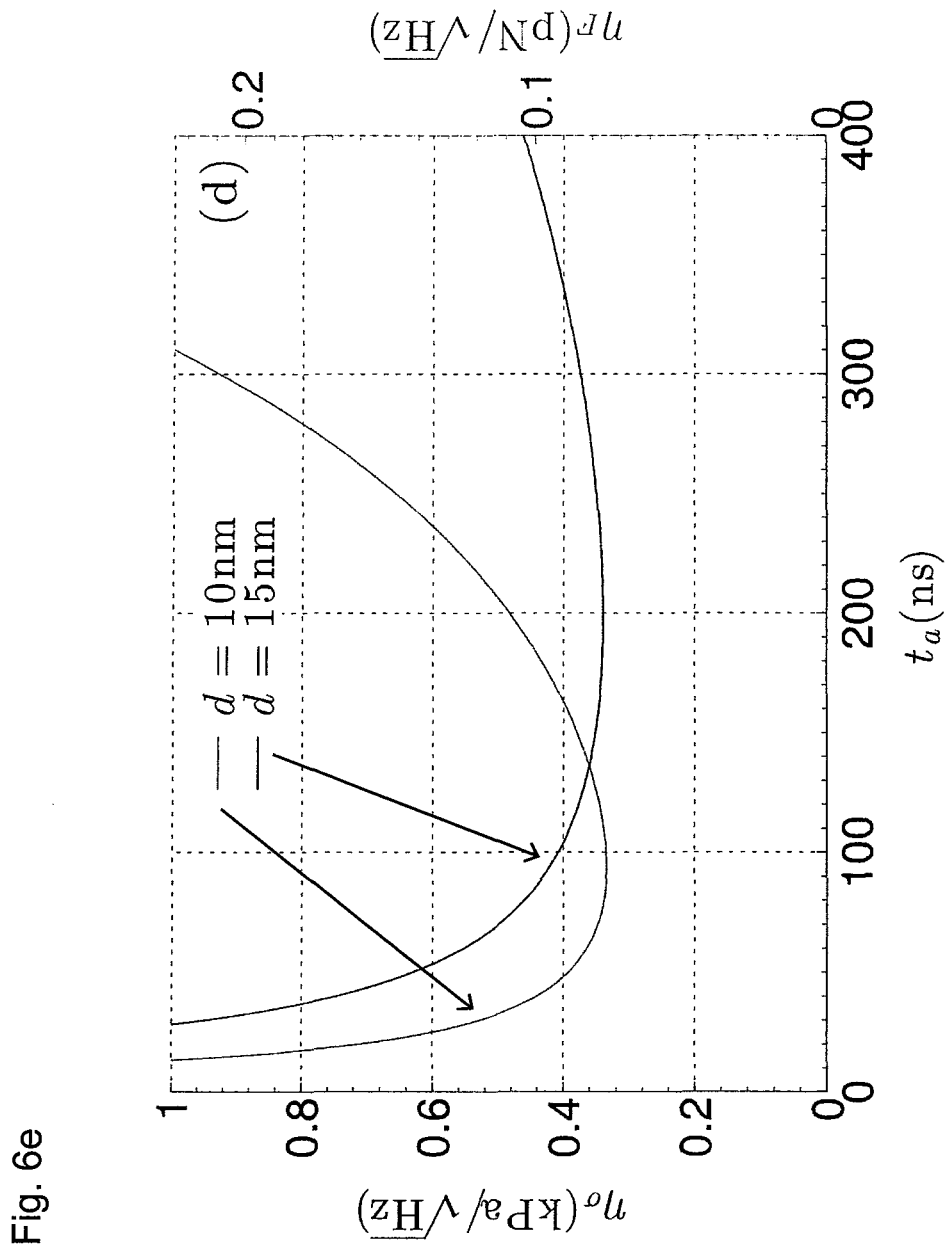
FIG. 6e shows the shot-noise-limited sensitivity for the measurement of stress and force as a function of interrogation time.

FIG. 6e shows the shot-noise-limited sensitivity for the measurement of stress (and force) within the total experiment time of 1 second as a function of interrogation time $t_a$.

$$\eta_{\sigma,t_a,T} = \frac{\sqrt{(3+\chi_\perp^2(t_a))(5-\chi_\perp^2(t_a))}}{8\pi C\chi_\perp(t_a)\chi_\parallel(t_a)t_a\left(\frac{d\Delta}{d\sigma}\right)}\sqrt{\frac{t_a+t_p}{T}} \quad (6)$$

The value of C is 0.3, the NV spin preparation and readout time is $t_p=600$ ns. The other parameters are the same as in FIG. 6c.

Measurement of Temperature with Colour Centres in Diamond and Piezo Element

In a method of the invention, a hybrid device that consists of a synthetic diamond layer formed by chemical vapour deposition (CVD) doped with NV centres during growth, a piezomagnetic element layer, and a thermal sensitive element island on a substrate, measures temperature. A change of temperature induces the expansion of the thermal sensitive element island with a thermal expansion constant $\varepsilon_T$, which can be as high as $2.3 \times 10^{-5}$ $K^{-1}$ (Aluminium), and $1.2 \times 10^{-5}$ $K^{-1}$ (Steel). The thermal expansion generates a stress acting on the attached piezomagnetic layer $\sigma_T = \varepsilon_T \cdot Y$, where Y denotes the Young's modules of the thermal sensitive material, $Y = 7 \times 10^4$ MPa (Aluminium), and $2 \times 10^5$ MPa (Steel). The sensitivity for the measurement of temperature thus reaches $$\eta_T = \eta_\sigma / (\varepsilon_T \cdot Y) \qquad (7)$$

The sensitivity for the measurement of pressure of $\eta_\sigma \sim 0.25$ kPa $Hz^{-1/2}$ implies the sensitivity for the measurement of electric field $\eta_E \sim 0.25$ mk $Hz^{-1/2}$.

The features described in the above description, claims and figures can be relevant to the invention in any combination.

REFERENCE NUMBER LIST 1, 2, 3, 4, 5, 6, 7, 8 Sensor
9 Diamond substrate layer
10 Piezomagnetic primary element layer
11 Piezoelectric primary element layer
12 Piezoelectric secondary element island
13 Thermally sensitive secondary element island
14 Permanent magnet
15 Colour centre
16 (Typically green) laser light
17 Fluorescence light
18 Photo detectors
19 Sensor array
20 Common substrate
21 Rotation and translation stages

The invention claimed is:

1. A sensor comprising a first diamond substrate with at least one colour centre, wherein the sensor further comprises a first piezomagnetic or piezoelectric primary element, which primary element is arranged to interact with the colour centre(s) of the first diamond substrate solely by means of either a stray electric field or stray magnetic field produced by the primary element.

2. The sensor according to claim 1, wherein the sensor comprises several diamond substrates, each substrate comprising at least one colour centre.

3. The sensor according to claim 1, wherein the sensor comprises several primary piezomagnetic or piezoelectric elements arranged to interact with colour centre(s) of the diamond substrate(s).

4. The sensor according to claim 1, wherein the colour centre(s) is/are nitrogen vacancy centre(s).

5. The sensor according to claim 1, wherein the primary piezomagnetic or piezoelectric element(s) is/are arranged to interact with the colour centre(s) of the substrate(s) magnetically or electrically.

6. The sensor according to claim 1, wherein the primary element(s) is/are piezomagnetic element(s) comprising a solid ferrite material.

7. The sensor according to claim 1, wherein at least part of the first primary element extends as a layer across at least part of a surface of the first diamond substrate.

8. The sensor according to claim 1, wherein the sensor further comprises a first secondary element which is arranged to interact with the first piezomagnetic or piezoelectric primary element.

9. The sensor according to claim 8, wherein the sensor comprises several secondary elements, each arranged to interact with the primary element(s).

10. The sensor according to claim 8, wherein the first secondary element forms an island in or on the first primary element.

11. The sensor according to claim 8, wherein the secondary element(s) is/are piezoelectric.

12. The sensor according to claim 8, wherein the secondary element(s) is/are thermally sensitive.

13. A method in which a change in a first piezomagnetic or piezoelectric primary element is detected by means of detecting a corresponding change in at least one colour centre of a first diamond substrate, which colour centre(s) interact with the first primary element solely by means of either a stray electric field or stray magnetic field produced by the first primary element.

14. The method of claim 13, wherein the change in at least one colour centre is a change in an electric spin of the colour centre(s).

15. The method of claim 13, wherein the method involves optical detection of the magnetic resonance of the colour centre(s).

16. The method of claim 14, wherein the electric spin is polarized by means of optical pumping.

17. The method of claim 13, wherein the change in the colour centre(s) detected is the chance in the colour centre (s)' fluorescence.

18. The method of claim 14, wherein the spins are measured with a pulse sensing scheme which is achieved by a microwave field.

19. The method of claim 13, wherein the colour centre(s) are exposed to a microwave field.

20. The method of claim 13, wherein the change in a first piezomagnetic or piezoelectric primary element is induced by a force or a change in a force applied to the first piezomagnetic or piezoelectric primary element.

* * * * *